(12) United States Patent
Capron et al.

(10) Patent No.: US 9,789,456 B2
(45) Date of Patent: Oct. 17, 2017

(54) COMPOSITION COMPRISING AN INTERNAL PHASE DISPERSED IN A HYDROPHILIC CONTINUOUS PHASE

(71) Applicant: INSTITUT NATIONAL DE LA RECHERCHE AGRONOMIQUE—INRA, Paris (FR)

(72) Inventors: Isabelle Capron, Nantes (FR); Herve Bizot, Suce-sur-erdre (FR); Bernard Cathala, La Chapelle sur Erdre (FR)

(73) Assignee: INSTITUT NATIONAL DE LA RECHERCHE AGRONOMIQUE—INRA, Paris (FR)

( * ) Notice: Subject to any disclaimer, the term of this patent is extended or adjusted under 35 U.S.C. 154(b) by 0 days.

(21) Appl. No.: 14/436,099

(22) PCT Filed: Oct. 15, 2013

(86) PCT No.: PCT/FR2013/052465
§ 371 (c)(1),
(2) Date: Apr. 16, 2015

(87) PCT Pub. No.: WO2014/060697
PCT Pub. Date: Apr. 24, 2014

(65) Prior Publication Data
US 2015/0273420 A1 Oct. 1, 2015

(30) Foreign Application Priority Data
Oct. 16, 2012 (FR) ...................... 12 59867

(51) Int. Cl.
*A61K 31/722* (2006.01)
*A61K 8/06* (2006.01)
*A61K 9/107* (2006.01)
*B01F 17/00* (2006.01)
*C08J 9/28* (2006.01)
*C08J 9/30* (2006.01)

(52) U.S. Cl.
CPC ............. *B01F 17/005* (2013.01); *C08J 9/28* (2013.01); *C08J 9/30* (2013.01); *C08J 2201/028* (2013.01); *C08J 2201/052* (2013.01); *C08J 2305/08* (2013.01)

(58) Field of Classification Search
None
See application file for complete search history.

(56) References Cited

U.S. PATENT DOCUMENTS 4,336,070 A 6/1982 Koshugi
6,365,642 B1 4/2002 Dyer et al.
2003/0134918 A1* 7/2003 Ko .................... A61K 31/00 521/50
2003/0211069 A1* 11/2003 Deckner ............. A61K 8/046 424/70.16
2010/0261803 A1 10/2010 Bismarck et al.

FOREIGN PATENT DOCUMENTS

| CN | 101020739 A | 8/2007 |
| CN | 102391416 A | 3/2012 |
| WO | 2010058148 A1 | 5/2010 |
| WO | 2012017160 A1 | 2/2012 |

OTHER PUBLICATIONS

International Search Report, dated Jan. 17, 2014, from corresponding PCT application.
Database WPI, Week 200835, Thomson Scientific, London, GB; XP002692991.
Database WPI, Week 201242, Thomson Scientific, London, GB; XP002692992.
Tzoumaki et al., "Oil-In-Water Emulsions Stabilized by Chitin Nanocrystal Particles", Food Hydrocolloids, vol. 25, Aug. 1, 2011, pp. 1521-1529.
Li et al., "Emulsion Stabilized by Starch Nanocrystals", Starch/Starke, vol. 64, Jun. 1, 2012, pp. 497-502.
Tan et al., "Fabrication of Starch-Based Nanospheres to Stabilize Pickering Emulsion", Carbohydrate Polymers, vol. 88, Feb. 16, 2012, pp. 1358-1363.
Gurevitch et al., "Polymerized Pickering HIPEs; Effects of Synthesis Parameters on Porous Structure", Journal of Polymer Science, Part B: Polymer Physics, vol. 48, Apr. 1, 2010, pp. 1516-1525.
Kalashnikova et al., "New Pickering Emulsions Stabilized by Bacterial Cellulose Nanocrystals", vol. 27, May 23, 2011, pp. 7471-7479.
Menner et al., "Tough Reinforced Open Porous Polymer Foams via Concentrated Emulsion Templating", vol. 47, No. 22, Oct. 18, 2006, pp. 7628-7635.
Brun et al., "Hybrid foams, colloids and beyond: From design to applications," Chemical Society Reviews, vol. 40, 2011, pp. 771-788.
Cameron, "High internal phase emulsion templating as a route to well-defined porous polymers," Polymers, vol. 46, 2005, pp. 1439-1449.

\* cited by examiner

Primary Examiner — Robert T. Crow
Assistant Examiner — John P Nguyen
(74) Attorney, Agent, or Firm — Young & Thompson

(57) ABSTRACT

The composition, advantageously an emulsion or a foam, includes an internal phase dispersed in a hydrophilic continuous phase, the percentage of the internal phase being higher than 50%. The emulsion composition contains nanocrystals of a polysaccharide other than cellulose, advantageously chitin, that are located at the interface between the internal phase and the hydrophilic continuous phase.

18 Claims, 3 Drawing Sheets

COMPOSITION COMPRISING AN INTERNAL PHASE DISPERSED IN A HYDROPHILIC CONTINUOUS PHASE

FIELD OF THE INVENTION

The present invention relates to the field of elevated internal phase compositions, advantageously, an emulsion or a foam, preferably, a so-called "medium internal phase" or "high internal phase" emulsion.

BACKGROUND ART

Some compositions comprise an internal phase dispersed in a continuous phase, namely in particular, emulsions and foams.

An emulsion is a mixture of, macroscopically homogenous but microscopically heterogeneous, two non-miscible liquid substances.

The involved two liquid substances are called phases. One phase is continuous; the other discontinuous internal phase is dispersed in the first phase as droplets.

Foam is very similar to emulsion: the gas (often air) is dispersed as many bubbles (it is referred to as a "dispersed phase" or "internal phase"), while the aqueous liquid is fully continuous (it is referred to as a "continuous phase").

Some of these compositions consist in immiscible dispersed systems in which the internal phase, also called dispersed phase, has a volume of greater than about 50 percent of the total volume of the composition.

Elevated internal phase emulsions conventionally consist in the so-called "medium internal phase" or "high internal phase" emulsions, also referred to as emulsions of the "MIPE" (Medium Internal Phase Emulsions) or "HIPE" (High Internal Phase Emulsions) type, respectively.

High internal phase emulsions or HIPE consist in liquid/liquid immiscible dispersed systems in which the internal phase has a volume greater than about 74%-75% of the total volume of the emulsion, i.e. a volume greater than what is geometrically possible for the compact packing of monodispersed spheres.

In turn, the medium internal phase emulsions or MIPE consist in liquid/liquid immiscible dispersed systems in which the internal phase has a volume ranging between about 50% and 74%-75% of the total volume of the emulsion.

The production of emulsions of the elevated internal phase water-in-oil type (of the MIPE or HIPE type), and their use for the manufacture of polymer foams, is for example described in the PCT application n° WO-2010/058148.

In this PCT application n° WO-2010/058148, the high internal phase emulsion is stabilized by cellulose or chitin-derived particles which, for that, are surface functionalized by hydrophobization.

However, the use of such transformed particles is likely to cause security concerns, especially for food applications, with their safety issues for the consumer.

Obtaining such transformed particles requires an additional step of surface modification.

In addition, these transformed particles are not suitable for the hydrophobic constituent encapsulation because they are intended for water-in-oil type emulsions.

In view of the above, there is a need for new elevated internal phase emulsion compositions of the oil-in-water type, for various industrial applications, especially food application.

More generally, there is a need for elevated internal phase compositions, especially emulsions, that are stabilized by agents available in large quantities, biodegradable, non toxic, renewable, of low cost and of very low densities and optionally, readily adaptable by surface modification.

SUMMARY OF THE INVENTION

The present invention relates to a composition (advantageously an emulsion or a foam) comprising an internal phase, especially hydrophobic or gaseous, dispersed in a hydrophilic continuous phase, the percentage of the internal phase being higher than 50%.

This composition is characterized in that it contains nanocrystals of a polysaccharide other than cellulose, located at the interface between said internal phase and said continuous phase.

The composition according to the invention contains thus advantageously:

(i) nanocrystals derived from a single polysaccharide or at least two different polysaccharides, excluding cellulose nanocrystals, or (ii) nanocrystals derived from a single polysaccharide or at least two different polysaccharides, other than cellulose, in combination with nanocrystals derived from cellulose.

The polysaccharide nanocrystals, other than cellulose nanocrystals, are advantageously selected from nanocrystals which are positively charged, i.e. preferably, chitin nanocrystals.

These polysaccharide nanocrystals are preferably selected from:

(i) exclusively positively charged polysaccharide nanocrystals, excluding cellulose nanocrystals, or (ii) positively charged polysaccharide nanocrystals, other than cellulose, mixed with nanocrystals derived from at least a negatively charged polysaccharide.

Such a composition advantageously consists in an emulsion or a foam.

The composition advantageously consists in an emulsion composition of the high internal phase or HIPE type, the percentage of the internal phase being higher than 75%.

Alternatively, the emulsion composition is of the medium internal phase or MIPE type, having a percentage of internal phase ranging between 50% and 75%.

The invention further relates to a product obtained from a composition according to the invention, selected from dry emulsion, solid foam, porous polymer material or polymer material beads.

The present invention further relates to a process for obtaining a composition comprising an internal phase, especially hydrophobic or gaseous, dispersed in a hydrophilic continuous phase, having a percentage of internal phase higher than 50%.

This process is characterized in that it comprises the following operations:

a) a step of incorporating nanocrystals of a polysaccharide other than cellulose, in a hydrophilic phase, (b) an operation of providing said hydrophilic phase containing the polysaccharide nanocrystals and a phase for constituting the internal phase, particularly a hydrophobic internal phase, c) an operation of forming said composition by dispersing said internal phase in said hydrophilic phase.

The polysaccharide nanocrystals incorporated in step a) are advantageously selected from nanocrystals which are positively charged, i.e. preferably chitin nanocrystals.

These polysaccharide nanocrystals are especially selected from:

(i) exclusively positively charged polysaccharide nanocrystals, excluding cellulose nanocrystals, or (ii) positively charged polysaccharide nanocrystals, other than cellulose, mixed with nanocrystals derived from at least a negatively charged polysaccharide.

At the end of the step c), the composition obtained advantageously consists in an emulsion or a foam.

According to a first embodiment, the operation c) of forming an emulsion consists in a "sequential" operation which comprises:

c.1) a step of obtaining an intermediate oil-in-water emulsion having a volume ratio hydrophobic internal phase/hydrophilic continuous phase of at least 5/95, c.2) a step of obtaining the emulsion composition having a percentage of internal phase higher than 50%, comprising:

c.2.1) a step of adding a volume of hydrophobic phase to the intermediate emulsion obtained in step c.1), and stirring the mixture thus obtained, and/or c.2.2) a step of concentrating the intermediate emulsion obtained in step c.1) by removing at least a part of said hydrophilic phase.

In this case, in step c.1), the intermediate oil-in-water emulsion has advantageously a percentage of internal phase that is equal to or less than 50%.

According to a second embodiment, the operation c) of forming an emulsion is advantageously a "direct" operation, which consists in mixing hydrophilic phase containing the polysaccharide nanocrystals and the hydrophobic phase to directly obtain said emulsion having a percentage of internal phase higher than 50%.

Generally, at the end of step c), the emulsion composition formed is (i) of the high internal phase or HIPE type, having a percentage of internal phase higher than 75%, or (ii) of the medium internal phase or MIPE type, having a percentage of internal phase ranging between 50% and 75%.

DETAILED DESCRIPTION OF THE INVENTION

Figure 1:
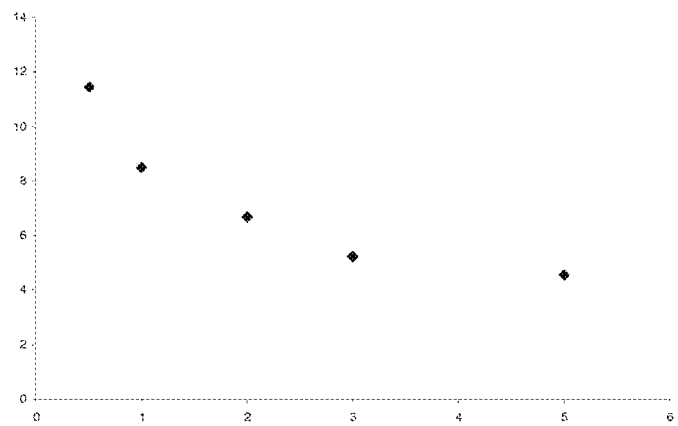
FIG. 1: Drop diameter distribution (μm) as a function of the chitin nanocrystal concentration in the aqueous phase (g/L)

The present invention provides a new elevated internal phase composition, that is to say advantageously a medium internal phase (MIPE) or high internal phase (HIPE) emulsion composition, as well as processes for obtaining the same.

Generally, the applicant showed that, unexpectedly, an emulsion composition of the MIPE/HIPE type can be stabilized by nanocrystals of a polysaccharide other than cellulose.

The applicant also showed that, unexpectedly, a composition in a foam form can be stabilized by nanocrystals of a polysaccharide other than cellulose.

Polysaccharide nanocrystals other than cellulose nanocrystals advantageously have the following benefits:

an irreversible adsorption resulting in a high stability of the MIPE/HIPE emulsions (the unfastening energy required for the desorption of nanocrystals from the interface is such that it is considered that this desorption does not occur spontaneously), non toxicity, biodegradable, from a biological source, and readily modified by post-treatment.

These nanocrystals of polysaccharide other than those of cellulose advantageously have an anisotropic rod type structure which ensures varying percentages of covering and porosity.

More preferably, the nanocrystals of polysaccharide other than those of cellulose are advantageously selected from nanocrystals obtained from polysaccharides comprising monomers of glucose or glucose derivative (for example glucosamine or glucosamine derivative), linked by beta 1,4 bonds.

The selected polysaccharide nanocrystals advantageously have an adaptable positive charge (while most of the biopolymers are negatively charged), allowing original and multiple combinations.

Composition According to the Invention

The composition according to the invention thus comprises an internal phase dispersed in a hydrophilic continuous phase, the percentage of the internal phase being higher than 50%.

This composition contains nanocrystals of a polysaccharide other than cellulose; these nanocrystals are located at the interface between the internal phase and the hydrophilic continuous phase.

Such a composition advantageously consists in:

an emulsion composition of the medium internal phase (MIPE) or high internal phase (HIPE) type, in which said internal phase is constituted by a hydrophobic liquid phase, or a composition in a foam form, in which said internal phase is constituted by a gaseous phase.

General Definition

The composition according to the invention advantageously consists in an emulsion or a foam.

By "emulsion" or "emulsion composition", it is meant a macroscopically homogenous but microscopically heterogeneous mixture of two non-miscible liquid phases.

In the present description, the notions of "emulsion" or "emulsion composition" are used interchangeably.

In an emulsion of the "oil-in-water" type, in the sense of the invention, (i) the hydrophilic dispersing continuous phase consists in an aqueous phase and (ii) the dispersed internal phase is a hydrophobic phase.

An oil-in-water emulsion may also be referred to as "O/W" in the present description.

By "foam", it is meant a complex medium comprised of a solid or liquid material thoroughly mixed with gas.

According to the invention, the foam advantageously consists in an aqueous liquid foam in which (i) the hydrophilic dispersing continuous phase consists in an aqueous phase and (ii) the dispersed internal phase is a gaseous phase.

This foam may consist in so-called "dry" foam, i.e. poorly hydrated foam.

More specifically, a foam is a "dry" one when the liquid only occupies a negligible part of the total volume of the foam; by convention, it is thus assumed that the volume fraction of liquid is then null.

Experimentally, the volume fraction of liquid can drop to $10^{-2}$ or $10^{-4}$.

The volume fraction of liquid corresponds to the ratio between the liquid volume and the total volume of foam ($V_{liquid}/V_{foam}$).

This value is related to the foam density $\rho$ by the following formula:

$$\rho = \rho_l \phi_l + \rho_g (1-\phi_l)$$

with
$\rho_l$ and $\rho_g$, the respective densities of the solution and the gas,
$\phi_l$ corresponding to the volume fraction of liquid,
$\phi_l^*$ corresponding to the critical volume fraction of liquid, the drops of which are not deformed (this notion is further defined in "Les mousses: structure et dynamique", L. Cantat et al. Paris; Ed Belin, 2010-278 pages—ISBN: 978-2-7011-4284-5).

3 types of foam structures are thus defined:
if $\phi_l^* < \phi_l$: the bubbles are spherical and without contact, corresponding to a bubbling liquid,
if $0.05 < \phi_l < \phi_l^*$: the bubbles are touching and are in form of crushed spheres, corresponding to a wet foam,
if $\phi_l < 0.05$: the bubbles are touching and are in form of polyhedrons, corresponding to a dry foam.

In other words, the percentage of internal phase is between about 64% and 95% for wet foam; the internal phase volume fraction is beyond 95% for dry foam.

The technical aspects of these foams are further described in the following document: "Les mousses: Structure et dynamique", L. Cantat et al. Paris; Ed Belin, 2010-278 pages—ISBN: 978-2-7011-4284-5).

In the present description, the terms "oil phase" and "hydrophobic phase" can be used interchangeably to refer to the oil liquid used for preparing an emulsion of the oil-in-water type.

The composition according to the invention comprises at least one internal phase.

In the present description, except the aspects specific to the emulsions, the terms "internal phase", "hydrophobic internal phase", "dispersed phase", "hydrophobic dispersed phase" can be used interchangeably to refer to:
the dispersed oil phase of an emulsion of the oil-in-water type, or
the gas dispersed in an aqueous liquid foam.

In the present description, the terms "aqueous phase" and "hydrophilic phase" can be used interchangeably to refer to the aqueous liquid used for preparing an emulsion of the oil-in-water type or a foam.

In the present description, the terms "continuous phase", "hydrophilic continuous phase" and "continuous aqueous phase" can be used interchangeably to refer to the dispersing aqueous phase of an oil-in-water emulsion or a foam.

By "percentage of internal phase" of an emulsion composition or foam, it is meant according to the invention, the ratio, as a percentage by volume, between (i) the volume of internal phase dispersed in the hydrophilic continuous phase and (ii) the total volume of the resulting composition.

For a foam, the notion of "percentage of internal phase" advantageously corresponds, equivalently, to the notion of "volume fraction of the dispersed phase".

A "elevated internal phase" composition is thus a liquid/liquid or liquid/gas immiscible dispersed system in which the internal phase, also called dispersed phase, occupies a volume higher than about 50%, preferably about 55%, of the total volume of the composition.

A "elevated internal phase emulsion" is thus a liquid/liquid immiscible dispersed system in which the internal phase, also called dispersed phase, occupies a volume higher than about 50%, preferably about 55%, of the total volume of the emulsion.

It is recalled that a high internal phase emulsion (HIPE) consists in a liquid/liquid immiscible dispersed system in which the internal phase, also called dispersed phase, has a volume higher than about 74-75 percent of the total volume of the emulsion, i.e. a volume higher than what is geometrically possible for the compact packing of monodispersed spheres, i.e. a sphere population of homogeneous size.

It is still recalled that a medium internal phase emulsion (MIPE) consists in a liquid/liquid immiscible dispersed system in which the internal phase has a volume of between 50 and 74-75 percent of the total volume of the emulsion.

According to the invention, the medium internal phase emulsion (MIPE) advantageously consists in a liquid/liquid immiscible dispersed system in which the internal phase has a volume of between 50, preferably 55, and 74-75 percent of the total volume of the emulsion.

In some situations, when a HIPE-type emulsion is prepared in accordance with the process defined above, an emulsion phase comprising the hydrophobic phase which is dispersed in the hydrophilic continuous phase can be obtained as an emulsion, with optionally (i) an oil phase consisting of a volume of the hydrophobic phase which is present in the composition in a non-dispersed form (this volume being measured) and/or (ii) an aqueous phase (not being part of the emulsion).

The percentage of internal phase is calculated by (i) measuring the volume of the non-dispersed hydrophobic phase, which phase generally surmounts the emulsion phase, (ii) measuring the volume of the emulsion phase, and then (iii) calculating the volume of the hydrophobic phase which is in dispersed form in the emulsion phase, on the understanding that the total volume of the hydrophobic phase contained in the composition is known.

By "volume ratio hydrophobic internal phase/hydrophilic continuous phase", especially for a MIPE or HIPE-type emulsion, it is meant according to the invention, the ratio between (i) the volume of the hydrophobic phase integrated in the emulsion, and (ii) the volume of the hydrophilic phase integrated in the emulsion.

This latter ratio is only indicative, in that it also depends on the amount of nanocrystals integrated in the emulsion. Generally, the tests were carried out with a hydrophilic phase containing suspended nanoparticles at a concentration of 0.3 to 0.8 g/L. This concentration is in no way limiting; the most reliable limit is advantageously, with no limitation, a covering rate of 80% during the manufacture of the Pickering emulsion. In the case of a "sequential" manufacturing process developed below, if the Pickering emulsion stability condition is met (step c.1)), the process can be continued by adding the hydrophobic phase or by withdrawing at least one portion of the hydrophilic phase to form the emulsion MIPE or HIPE (step c.2)).

Percentage of Internal Phase

According to the invention, a composition comprising "elevated internal phase" has a percentage of internal phase higher than 50%, preferably, higher than 55%.

According to an embodiment, the emulsion formed is advantageously of the medium internal phase (MIPE) type, having a percentage of internal phase between 50% and 75%, preferably between 55% and 75%, still advantageously between 60% and 75%, still advantageously between 65% and 75% and still advantageously between 70% and 75%.

According to another embodiment, the emulsion formed can be further of the high internal phase (HIPE) type, having a percentage of internal phase higher than 75%, preferably higher than 80%, more preferably higher than 85%, or even higher than 90%. This percentage of internal phase ranges still advantageously between 80% and 90%, preferably between 85% and 90%.

According to still another embodiment, the composition is in a foam form, the internal phase percentage of which, corresponding to the volume fraction of the dispersed phase, is higher than 50%, preferably higher than 55%, even preferably, between 64% and 95%.

In the case of the so-called "dry" foam, the percentage of internal phase is advantageously higher than 95%.

Volume Ratio

In some embodiments, a MIPE or HIPE emulsion composition having a volume ratio hydrophobic internal phase/hydrophilic continuous phase higher than 60/40, more preferably higher than 80/20, is formed.

By "higher than 60/40" or "of at least 60/40", it is meant a hydrophobic internal phase having a value advantageously higher than 60 in the volume ratio, namely including 65/35, 70/30, 75/25, 80/20, 85/15 or 90/10.

By "higher than 80/20" or "of at least 80/20", it is meant a hydrophobic internal phase having a value advantageously higher than 80 in the volume ratio, namely including 85/15 or 90/10.

Nanocrystals of a Polysaccharide Other than Cellulose

The composition, especially, an emulsion composition, is thus stabilized by nanocrystals of polysaccharide which consist, at least for some of them, in nanocrystals other than nanocrystals of cellulose.

Polysaccharides (sometimes referred to as complex glycans, polyosides, polyholosides or carbohydrates) are polymers consisting of several oses (also called sugars or anhydroglucose unit or AGU) bond together.

By "polysaccharides", it is meant, in particular, polymers formed by the repeated condensation of oses, by osidic linking of advantageously at least 10 osidic units, to achieve several hundreds or thousands of units.

Polysaccharide nanocrystals are known in the prior art, frequently under the name of "whiskers" or "nanowhiskers".

The term "nanocrystals" means that these are crystals whose at least one dimension is of nanoscopic or submicron size, comprising of macromolecular chains oriented along the direction of the fiber in parallel or anti-parallel.

Such polysaccharide nanocrystals may be obtained from various sources, for example of vegetable, bacterial, animal, fungal or amoebic origin; they can be obtained by degradation of the source or by recrystallization.

The composition according to the invention may contain especially:
(i) nanocrystals derived from a polysaccharide or a mixture of polysaccharides other than cellulose, or
(ii) nanocrystals derived from a polysaccharide or a mixture of polysaccharides other than cellulose, blended with nanocrystals derived from cellulose.

By "cellulose nanocrystals", it is meant nanocrystals known in the prior art, frequently under the name of cellulose "whiskers", cellulose "nanowhiskers" or "nanocellulose".

Such cellulose nanocrystals may be obtained from various sources: vegetable (for example wood pulp, cotton or algae), animal (for example tunicate), bacterial, regenerated cellulose or mercerized cellulose. They are for example described in Samir et al. (2005, Biomacromolecules, Vol. 6: 612-626) or in Elazzouzi-Hafraoui et al. (Biomacromolecules. 2008; 9(1):57-65).

Nanocrystals of polysaccharide other than that of cellulose are advantageously selected from nanocrystals obtained from the so-called "structural-type" polysaccharides, i.e. polymers of glucose or glucose derivative that are not branched and the linkage between unit of which is a β-type anomeric linkage.

In this regard, nanocrystals of polysaccharide other than that of cellulose are advantageously selected from nanocrystals obtained from the following polysaccharides:
from glucans, polymers of D-glucose,
from galactans, polymers of D-galactose,
from xylans, polymers of D-xylose, and
from polymers of D-glucosamine, comprising especially chitin.

By "glucan", it is meant the α-glucan family, including the following polysaccharides:
starch, α-1,4- and α-1,6-glucan
amylopectin, α-1,4- and α-1,6-glucan
amylose, α-1,4-glucan.

By "glucan", it is also meant the β-glucan family, including the following polysaccharides:
curdlan, β-1,3-glucan
laminarin, β-1,3- and β-1,6-glucan
lentinan, pure β-1,6: β-1,3-glucan
pamylon
pleuran, β-1,3- and β-1,6-glucan
zymosan, β-1,3-glucan More preferably, these nanocrystals of polysaccharide other than that of cellulose are advantageously selected from nanocrystals obtained from polysaccharides comprising monomers of glucose or glucose derivative (for example glucosamine or glucosamine derivative, including of the N-acetyl-D-glucosamine type), connected by beta 1,4 linkages.

Among the polysaccharide nanocrystals, those comprising a positive charge are particularly selected (while most of the biopolymers are negatively charged), allowing original and multiple combinations.

This positive charge is advantageously adaptable.

This positive charge may be intrinsic to the nanocrystals of interest (non-functionalized particles) or can be obtained by functionalization (advantageously by grafting an N-acetylamine function).

The composition according to the invention may thus contain especially:
(i) exclusively positively charged polysaccharide nanocrystals, excluding cellulose nanocrystals, or
(ii) positively charged polysaccharide nanocrystals, other than cellulose, mixed with nanocrystals derived from at least one advantageously negatively charged polysaccharide.

In this regard, polysaccharide nanocrystals are thus advantageously selected from chitin nanocrystals, also generally referred to as "ChN".

The chemical name of the chitin molecule is poly-N-acetyl-D-glucosamine, β-(1,4)-2-acetamido-2-deoxy-D-glucose or more simply [N-acetyl-D-glucosamine β-(1,4)N-acetyl-D-glucosamine]$_n$.

The chitin includes advantageously polysaccharides comprised of N-acetyl-β-D-glucosamine units (from 50 to 100%) and D-glucosamine units (from 0 to 50%).

In the context of the invention, are advantageously named "chitin nanocrystals", acicular crystalline articles composed of an association of glucosamine copolymer chains and N-acetyl-D-glucosamine linked by a β (1-4) linkage.

Chitin nanocrystals can be of animal or fungal origin. Examples of animal source include crustaceans (crab, shrimp, lobster, etc.) and some insects (cockchafer, beetle, etc.). Examples of fungal source of chitin include fungi and yeasts.

As developed afterwards, the applicant showed that the physicochemical properties of a MIPE/HIPE-type emulsion composition stabilized by chitin nanocrystals are conditioned by the following parameters:
  structural parameters of the chitin nanocrystals,
  charge density on the surface of the chitin nanocrystals,
  rate of covering by the chitin nanocrystals,
  volume ratio hydrophobic dispersed phase/hydrophilic continuous phase,
  ionic strength or pH of the emulsion composition, and
  preparation method.

As also developed afterwards, the applicant showed that the physicochemical properties of a foam-type composition stabilized by chitin nanocrystals are conditioned by the following parameters:
  rate of covering by the chitin nanocrystals,
  ionic strength or pH of the emulsion composition.

In particular, chitin nanocrystals present unexpectedly higher stabilization qualities (related to the presence of acetylamine functions the hydrophobic character of which strengthens the amphiphilic character bringing more easily these nanocrystals at the interface).

Nanocrystals can be also obtained from polysaccharides selected from β-1,3-glucan, β-1,3-xylan and β-1,4-mannan, which share a fibrillar structure similar to chitin. Thus, these polysaccharides can also have nanocrystals form.

These latter nanocrystals may be of vegetable or fungal origin. Examples of vegetable source include particularly, for the β-1,3-xylan, some algae. For the β-1,4-mannan, some algae can also be mentioned, as well as land plant seed endosperm. As example of polysaccharide fungal source, one can mention especially, for the β-1,3-glucan, some fungi and some yeasts.

Nanocrystals can be also obtained from polysaccharides selected from starch, α-1,4-glucan and α-1,6-glucan.

The composition according to the invention may thus advantageously contain:
  (i) chitin nanocrystals, exclusively, or
  (ii) chitin nanocrystals, advantageously positively charged, mixed with nanocrystals from at least another polysaccharide (for example cellulose) advantageously negatively charged.

According to a preferred embodiment of the case (i), the composition is only stabilized by chitin nanocrystals, without adding:
  other emulsifying or stabilizing compounds,
  or other solid particles, either said solid particles are functionalized or not.

According to the case (ii), the ratio positively charged chitin nanocrystals/nanocrystals from negatively charged polysaccharide(s) is advantageously adjusted based on the value corresponding to the desired surface charge.

This ratio can be selected for example between 1/99 and 99/1, preferably between 10/90 and 90/10, especially from 1/99, 10/90, 20/80, 30/70, 40/60, 50/50, 60/40, 70/30, 80/20, 90/10 or 99/1.

In this case, the surface of the drops or bubbles would be advantageously of the zwitterionic type (positive and negative).

The composition may further contain any other compound suitable for its use, final destination or application.

The application of the composition can be selected from compositions usable in food, cosmetic, pharmaceutical or phytosanitary fields.

Depending on the desired application of the final composition according to the invention, the composition may contain for example, but not limited to, active ingredients and adjuvants such as preservatives, gellants, solvents, coloring matters, etc.

Dimensional Characteristics of Polysaccharide Nanocrystals

Nanocrystals of polysaccharide, especially chitin, are highly crystalline solid particles.

These nanocrystals of polysaccharide are free of, or at least virtually free of, amorphous part. They have preferably a crystallinity of at least 60%, and preferably of between 60% and 95%.

Nanocrystals of polysaccharide, other than those of cellulose, are advantageously in the form of anisotropic rods (Revol J F and Marchessault R H, Int. J. Biol. Macromol. (15) 1993, 325), plates or spheres (spherulites) Murray S. B. and Neville A. C., Int. J. Biol. Macromol. 20 (1997) 123-130).

By "anisotropic rods", it is meant adjustable particles with a length/width ratio higher than 1.

This morphology can be observed for example by electron microscopy, particularly by transmission electron microscopy (or TEM).

These nanocrystals have advantageously widths ranging from 2 to 50 nm, for maximum lengths in the order of micron.

Advantageously, chitin nanocrystals have anisotropic elongated shape.

Chitin nanocrystals generally include the following dimensional characteristics: (i) a mean length between 150 and 600 nm, and (ii) a width between 5 and 50 nm.

As an exception, nanocrystals from chitin of the "rifia" (animal of deep sea) whose dimensional characteristics are: (i) a mean length in the order of 2200 nm, and (ii) a width in the order of 18 nm, are also known.

By "length", it is meant the larger dimension of the nanocrystals, separating two points at the end of their respective longitudinal axis.

By "width", it is meant the dimension measured along the nanocrystals, perpendicular to their respective longitudinal axis and corresponding to their maximum cross-section.

In preferred embodiments, chitin nanoparticles form a relatively homogenous population of nanocrystals, whose length experimental values follow a Gaussian distribution centered on the length value attributed to said nanocrystal population. In these preferred embodiments, for example chitin nanocrystals having a "single specified size" can be used, as illustrated in the examples.

In practice, nanocrystal morphology and dimensions can be determined using various imaging techniques such as transmission electron microscopy (TEM) or atomic force microscopy (AFM), small-angle X-ray scattering or small-angle neutron scattering (SAXS or SANS, respectively) or dynamic light scattering (DLS).

Advantageously, chitin nanocrystals have a length/width ratio of more than 1 and less than 100, preferably, between 5 and 30.

A length/width ratio of more than 1 and less than 100 includes the length/width ratios of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99.

For example, chitin nanocrystals can be obtained from:

crab shell: 240 nm by 15 nm (Nair and Dufresne, *Biomacromolecules* 2003) or 260±80 nm by 23±3 nm (Belamie et al. *J. Phys. Chem.* 2004), or shrimp shell: 200 to 560 nm by 18 to 40 nm (Phonggying et al. *Polymer* 2007).

Charge on the Surface of Polysaccharide Nanocrystals

In order to optimize the composition stability, polysaccharide nanocrystals are advantageously selected according to their surface characteristics, taking into account especially electrostatic aspects.

In particular, chitin nanocrystals are positively charged due to the surface amine functions (in particular, a N-acetylglucosamine moiety); the surface charge density then varies according to the acetylation level.

Regarding the surface electrostatic characteristics, the emulsion stabilizing chitin nanocrystals advantageously have maximum surface charge density in the order of 1 $e \cdot nm^{-2}$. It is noted that "e" is an elementary charge.

Surface charge density can be optionally selected according to the ionic strength of the aqueous phase.

The destabilizing effect of the surface charge density can be optionally annihilated by increasing ionic strength in the aqueous phase.

Advantageously, this surface charge density is determined by conductimetric dosing.

The desired surface charge density can be obtained by monitoring the nanocrystal acetylation level.

The "degree of acetylation" (or "DA") is the mole fraction×100 of the N-acetyl-D-glucosamine units by the glucosamine unit total number.

The DA can be determined by different methods: conductimetric titration, elementary analysis measurement of the nitrogen/carbon ratio, IR or UV spectrometry, 1H liquid or 13C solid NMR, or by enzyme reaction (M. Rinaudo, Progress in Polymer Science, 2006, 31, 603-632).

Chitin deacetylation may be carried out in alkaline condition (concentrated NaOH) or by enzymatic hydrolysis in the presence of chitin deacetylase.

It is possible to partially deacetylate chitin nanocrystals by an alkaline treatment, for example 33% NaOH solution at 90° C. for 2 h to 4 h with yields of from 85% to 90% (Y. M. Fan, T. Saito and A. Isogai, Carbohydrate Polymers, 2010, 79, 1046-1051).

The degree of acetylation (DA) defines the chain solubility and thus, its nomenclature.

For DAs higher than 50%, chitin is in insoluble solid form; for DAs lower than 50%, soluble chitosan chains are obtained.

According to the invention, this acetylation level is advantageously between 50% and 100%, preferably, at least 70% (for example around 74%), more preferably around 90%.

Generally, the polysaccharide nanocrystals used according to the invention are nanocrystals that have not undergone any surface function modifications.

This includes chitin nanocrystals the amine functions of which have not been modified by deacetylation.

Especially, polysaccharide nanocrystals that have not been functionalized or grafted with groups allowing their subsequent crosslinking, for example, groups of methacrylate or dimethacrylate type, are preferentially used.

Also, polysaccharide nanocrystals that have not been functionalized or grafted with polymer molecules, such as polyethylene glycol, poly(hydroxyester) or polystyrene, are preferentially used.

Generally, it would appear that there is an effect of the surface charge density in the absence of salt, but this effect disappears by adding NaCl (which shields charges and limits electrostatic repulsions).

Quantity of Polysaccharide Nanocrystals Other than Cellulose Nanocrystals and Covering Rate The composition comprises advantageously from 0.035% to 2% by weight, more preferably, from 0.05% to 1% by weight, of nanocrystals of polysaccharide, advantageously chitin, based on the total weight of said composition.

This polysaccharide nanocrystal mass proportion can be evaluated for example by dry extracting the aqueous phase or dosing sugars after hydrolysis.

It was shown according to the invention that an amount of polysaccharide nanocrystals sufficient to obtain a covering rate of at least 50%, preferably at least 60%, more preferably at least 70%, advantageously around 80%, based on the implemented nanocrystal type, is required for obtaining final MIPE or HIPE emulsion composition according to the invention.

In the sense of the present description, the "rate of covering" by polysaccharide nanocrystals represents the proportion of droplet surface of the hydrophobic phase dispersed in the aqueous phase, at the interface oil/water, which is covered by polysaccharide nanocrystals.

The covering rate "C", which is the ratio between (i) the surface of polysaccharide nanocrystals present in the emulsion composition capable of being stabilized at the interface hydrophobic internal phase/hydrophilic continuous phase and (ii) the total surface of the hydrophobic phase droplets in said emulsion composition, is calculated by the following formula (I):

$$C = S_p/S_d \qquad (I),$$

in which:

$S_p$ represents the polysaccharide nanocrystal surface capable of being stabilized at the interface present in the emulsion composition, and $S_d$ represents the total surface of the hydrophobic phase droplets in the emulsion composition.

The nanocrystal surface is assimilated to a single plane surface, with the assumption that nanocrystals are aligned with said surface into a planar ribbon.

Consequently, the nanocrystal surface value can be calculated by the following formula (II):

$$S_p = N_p Ll = \frac{m_p}{h \rho_p}, \text{ with:} \qquad (II)$$

$$N_p = \frac{m_p}{V_p \times \rho_p} = \frac{m_p}{L \times l \times h \times \rho_p}$$

in which:

$S_p$ represents the polysaccharide nanocrystal surface capable of being stabilized at the interface present in the emulsion composition, $N_p$ refers to the number of polysaccharide nanocrystals present in the aqueous phase, L refers to the length of the polysaccharide nanocrystals, l refers to the width of the polysaccharide nanocrystals, h refers to the height of the polysaccharide nanocrystals, $m_p$ refers to the mass of the polysaccharide nanocrystals, $\rho$ refers to the density of the polysaccharide nanocrystals.

The surface of the droplets is the surface at the interface oil/water, which was calculated for each droplet mean diameter along D(3,2).

Consequently, the droplet surface value can be calculated by the following formula (III):

$$S_d = 4\pi R^2 \times Ng = 4\pi R^2 \times \frac{3V_{oil}}{4\pi R^3} = \frac{3V_{oil}}{R}, \text{ with:} \quad (III)$$

$$N_g = \frac{V_{oil}}{4/3\pi R^3} \quad (IV)$$

in which:

Ng refers to the number of droplets present in the emulsion, $S_d$ refers to the droplet surface value of hydrophobic phase, R refers to the droplet mean radius, and $V_{oil}$ refers to the total volume of the hydrophobic internal phase.

The final value of the covering rate "C" is calculated by the formula (I) already mentioned above:

$$C = Sp/Sd \quad (I),$$

in which:

$S_p$ represents the polysaccharide nanocrystal surface capable of being stabilized at the interface present in the emulsion composition, $S_d$ represents the total surface of the hydrophobic phase droplets in the emulsion composition.

The examples further show that a composition in foam form can be obtained from a solution containing a concentration of at least 6 g/L of chitin.

Ionic Strength and pH

The applicant also showed that the emulsion composition stability can be increased by using an aqueous phase with a specified minimum ionic strength.

As shown in the examples with chitin nanocrystals, optimum stability of the emulsion is obtained from a minimum threshold of aqueous phase ionic strength value (for example a final concentration at 2 mM of NaCl for 3 g/L suspension of chitin nanocrystals and a HCl concentration of 0.01 mM).

As also shown in the examples, maximum stability of the emulsion composition is obtained for an ionic strength value corresponding to a final concentration of NaCl of from 10 to 50 mM in said emulsion.

Still as observed in the examples, the absence of ionic strength or an increase of ionic strength beyond 10 mM tends to a destabilization of a foam type composition. In this case, the ionic strength is advantageously between 1 and 5 mM of NaCl.

Without intending to be bound by any theory, the applicant thinks that the ionic strength threshold value of the aqueous phase from which the optimum stability of the emulsion is obtained is that for which charges (counter-ions) present in the aqueous phase neutralize charges (ions) present on nanocrystals.

As also shown in the examples, the presence of excess counter-ions does not significantly affect the emulsion stability properties. For a massive excess of counter-ions, which has not been achieved in the example operational conditions, a change of the conditions can be predicted due to nanocrystal precipitation without necessarily altering the emulsion stability (the aggregation phenomenon was found rather favorable for emulsion stabilization).

As an indication, according to a particular embodiment, chitin nanocrystals advantageously comprise maximum surface charge density of 0.9 $e \cdot nm^{-2}$ to stabilize a composition comprising an ionic strength at least equal to the ionic strength equivalent to 5 mM of NaCl.

For a composition comprising an ionic strength higher than the ionic strength equivalent to 10 mM of NaCl, surface charge density on the chitin nanocrystals seems no longer to be a relevant parameter for the effective stabilization of the emulsion.

An ionic strength higher than the ionic strength equivalent to 10 mM of NaCl includes an ionic strength higher than 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 275, 280, 290, 300, 310, 315, 320, 325, 330, 335, 340, 345, 350, 360, 370, 375, 380, 390, 400, 410, 420, 430, 440, 450, 460, 470, 480, 490, or higher than 500 mM of NaCl. Preferably, the ionic strength is lower than an ionic strength equivalent to 3 M of NaCl.

The applicant also showed that the emulsion composition stability can be increased by using an aqueous phase with a specified pH, the value of which is advantageously adjusted by the acid concentration.

For example, the acid is selected from mineral and organic acids, advantageously, from hydrochloric acid, perchloric acid, acetic acid, formic acid, chloroacetic acid, citric acid, picric acid, ascorbic acid, and fatty acids comprising up to 12 carbon atoms; hydrochloric acid is preferentially used.

As shown in the examples, maximum stability of the emulsion composition is obtained for a pH value between 3 and 6. Similarly, the pH increase from 3 to 5 promotes the stabilization of the composition in foam form.

Also in the examples, it is shown that foam formation is reversible as a function of the pH.

Emulsion Composition Structure

In order to define the structure of the emulsion composition, characteristics relating to the size distribution of the lipid droplets constituting the hydrophobic phase dispersed in the hydrophilic phase can be particularly used.

Example includes the most important in volume of its lipid droplet population, also named "mode", measured in μm.

Size distribution of lipid droplets can be characterized by the so-called "Sauter" diameter ($d_{3.2}$) and a $d_{4.3}$ value, defined respectively by the following formulas:

$$d_{3.2} = \Sigma n_i d_i^3 / \Sigma n_i d_i^2$$

$$d_{4.3} = \Sigma n_i d_i^4 / \Sigma n_i d_i^3$$

where $n_i$ is the number of lipid droplets of $d_i$ diameter.

These two values enable to better assess the size distribution of lipid droplets dispersed in the hydrophilic continuous phase.

This lipid droplet population is for example determined by the laser granulometry technique.

Internal Phase

The hydrophobic phase is selected from vegetable oils, animal oils, mineral oils, synthetic oils, hydrophobic organic solvents and hydrophobic liquid polymers.

The hydrophobic phase can be selected from substituted or unsubstituted alkane or cycloalkane. Examples illustrate embodiments of a HIPE emulsion according to the invention with alkanes and cycloalkanes, respectively.

For the hydrophobic phase, an alkane with more than 5 carbon atoms includes alkanes with more than 6, 7, 8, 9, 10, 11, 12, 13, 14, 15, 16 or more than 17 carbon atoms, i.e. especially, according to the conventional nomenclature, $C_6$-$C_{18}$ alkanes and which are of the formula $C_nH_{2n+2}$. Said alkanes can be linear or branched.

Said alkanes include linear or branched alkanes of the hexane, heptane, octane, nonane, decane, undecane, dodecane, tridecane, tetradecane, pentadecane, hexadecane, heptadecane and octadecane types.

Substituted alkanes include the above linear or branched alkanes at least one hydrogen atom of which is substituted by a halogen selected from chlorine, bromine, iodine or fluorine. The substitution of at least one hydrogen atom includes the substitution of 2, 3, 4 or 5 hydrogen atoms.

In some embodiments, said cycloalkane is a substituted or unsubstituted cyclohexane. The cyclohexane may be substituted by 1, 2, 3 or 4 halogen atoms selected from chlorine, bromine, iodine or fluorine.

The hydrophobic phase may also comprise a mixture of such alkanes, for example as paraffin oil.

In some embodiments, the hydrophobic phase comprises one or more polymerizable hydrophobic monomers of a known type.

In other embodiments, the hydrophobic phase consists essentially in a composition of a hydrophobic monomer or a mixture of hydrophobic monomers. As an illustration, the hydrophobic phase may consist essentially in a styrene monomer composition.

Embodiments in which the hydrophobic phase comprises, or consists in, a hydrophobic monomer or a combination of hydrophobic monomers, are particularly useful for the manufacture of polymeric material beads (by polymerizing these monomer(s)).

In the case of a foam, the internal phase consists in a gas, advantageously air, nitrogen or carbon dioxide.

Hydrophilic Phase

By "hydrophilic phase" or "aqueous phase", it is meant a liquid immiscible with the hydrophobic phase. A hydrophilic phase miscible with water is preferably used. The hydrophilic phase may be water, as shown in the examples.

The hydrophilic phase can be a hydrophilic solvent, preferably a solvent bearing hydroxyl groups, such as glycols. For the hydrophilic phase, glycols include glycerol and polyethylene glycols.

The hydrophilic phase can also contain water-soluble texturing agents, including thickening or viscosifying agents, such as polysaccharides (for example dextran or xanthan, the latter being widely used in food applications).

The hydrophilic phase can be, partially or totally, comprised of an organic liquid selected from an alcohol such as ethanol, or acetone.

The hydrophilic phase can comprise a single liquid or a mixture of several liquids.

The person skilled in the art can easily adapt the constitution of the hydrophilic phase, especially according to the final MIPE or HIPE emulsion that is desired.

In some embodiments, the hydrophilic phase may include various additional substances or combination of additional substances useful for the desired industrial application of the MIPE or HIPE emulsion, such as medicine active ingredients.

In some embodiments, the hydrophilic phase comprises one or more hydrophilic monomers which can be subsequently polymerized within the MIPE or HIPE emulsion.

In some embodiments, the hydrophilic phase comprises one or more polymerizable hydrophilic monomers of known type.

In other embodiments, the hydrophilic phase consists essentially in a composition of a hydrophilic monomer or a mixture of hydrophilic monomers. As an illustration, the hydrophilic phase may consist essentially in a composition of hydrophilic monomers of acrylate type.

Embodiments in which the hydrophilic phase comprises, or consists in, a hydrophilic monomer or a combination of hydrophilic monomers, are particularly useful for the manufacture of porous polymeric material.

Obtaining Process

The present invention also elates to process for obtaining the composition set forth above.

For the manufacture of a foam by dispersing a gas phase in the hydrophilic phase, it is possible to refer for example to the protocol described in document Lucassen, J. (1981) Lucassen-Reijnders, E. H. ed. Anionic Surfactants—Physical Chemistry of Surfactant Action NY, USA: Marcel Dekker, in document Alargova et al.—"Foam superstabilization by polymer microrods", Langmuir, vol. 20(24), 2004, 10371-10374, or in document Bianco E. et al., "Stability and Viscoelasticity of Magneto-Pickering Foams", Langmuir 29, (2013), 10019-10027.

Generally, several methods are possible to disperse a gas in a liquid, namely in essence, insufflate the gas in the liquid, manufacturing it in situ, beat the liquid in the presence of the gas or mix a gas and a liquid by passing them through a porous material.

In this case, particulate liquid hydrophilic foam, preferably, the so-called "dry" foam as described above, is advantageously obtained.

According to this application, the chitin nanocrystals have the specific interest of conferring to solution particularly interesting foamability properties.

The "foamability" or "foaming power" of a solution is a qualitative measurement of its ability to produce foam when it is shaken or when bubbles are injected there.

Surprisingly, the applicant also showed that MIPE or HIPE emulsions of the oil-in-water type having a high content of hydrophobic dispersed phase, higher than 50% or higher than 75% of the total volume of the emulsion, can be obtained "sequentially" (also referred to as in "two steps") from Pickering-type emulsions stabilized by nanocrystals of polysaccharide other than cellulose.

Pickering-type emulsions are known in the state of the art, and consist in emulsions that are stabilized by colloidal suspended particles located at the interface oil/water.

Generally, Pickering emulsions are free of conventional surfactant. In some embodiments, a Pickering emulsion can contain one or more conventional surfactants, but not enough to stabilize an emulsion.

Pickering emulsions, stabilized by nanocrystals of polysaccharide other than cellulose, which are used as starting product for obtaining MIPE or HIPE emulsions of the oil-in-water type disclosed in the present description, are specific to the present invention, and their preparation process is described in detail below.

More specifically, the applicant showed that, surprisingly, MIPE or HIPE emulsions of the above-mentioned type can be obtained when a Pickering oil-in-water emulsion stabilized by chitin nanocrystals is used as starting composition.

Notably, it was shown according to the invention that HIPE emulsions are obtained because Pickering emulsion compositions stabilized by chitin nanocrystals then allow to surpass the compact packing state of the hydrophobic internal phase (also called "close packing" state), i.e. to obtain an internal phase percentage higher than 75%.

On the other hand, the applicant further shows that chitin nanocrystals display the specific and unexpected property of directly allowing a elevated internal phase emulsion composition to be obtained (the so-called "direct" process), without requiring to pass through a Pickering type emulsion.

As shown hereinafter, in the case of emulsion compositions, the "direct" route integrates all of the hydrophilic phase introduced, while the "sequential" route tends to exclude hydrophilic phase, increasing the percentage of internal phase for the MIPEs. Beyond 74% of internal phase, the internal phase percentages are identical in the two processes.

The process according to the invention comprises advantageously the following operations:

a) a step of incorporating nanocrystals of a polysaccharide other than cellulose, advantageously chitin, in a hydrophilic phase, b) an operation of providing (i) said hydrophilic phase containing polysaccharide nanocrystals and (ii) a phase for constituting the internal phase (a hydrophobic liquid phase or a gas phase, as appropriate), c) an operation of forming said composition by dispersing said internal phase in said hydrophilic phase.

Generally, it was shown in the examples that the process for obtaining HIPE emulsions according to the invention enables the preparation of emulsion compositions with a high content of hydrophobic internal phase, having up to more than 95 vol % of hydrophobic internal phase.

It was also shown that MIPE or HIPE emulsions prepared according to the process of the invention and having a volume ratio hydrophobic internal phase/hydrophilic dispersed phase of more than 60% may be in the form of solid gel.

It was shown in the examples that MIPE or HIPE emulsion compositions prepared by the process of the invention are stable for a long period of time, in this case several months, including when they are stored at about 20° C.

Moreover, it was shown that MIPE or HIPE emulsions obtained in accordance with the process of the invention have an excellent compressive strength capability.

Also, the applicant showed the reversibility of the HIPE emulsion breaking according to the invention, for example, by shearing, (for example, by high stirring) or compression (for example, by high centrifugation). A HIPE emulsion according to the invention has therefore the property of forming again upon itself after breaking.

By studying HIPE emulsions of the invention with confocal scanning microscopy, it was observed that the oil drops dispersed in the continuous aqueous phase distort with the increasing ratios hydrophobic internal phase/hydrophilic dispersed phase, until conforming into polyhedrons, which minimizes the volume occupied by the continuous aqueous phase.

It was also shown that a HIPE emulsion according to the invention can be subjected to a treatment to achieve a dry emulsion, for example, when the hydrophobic internal phase is comprised of an oil less volatile than water, polymerizable or non-lyophilizable, and consequently, only the continuous aqueous phase is removed by drying or freeze-drying.

It was also shown that a HIPE emulsion according to the invention can be used to make dry foams, for example (i) either by freeze-drying said emulsion when both phases are lyophilizable, (ii) or when the hydrophobic dispersed phase comprises polymerizable monomers, by polymerizing said monomers and then removing the continuous aqueous phase.

Provision of Polysaccharide Nanocrystals

Some polysaccharides, especially chitin, consist of one part called "amorphous", while a second part is "crystalline".

Polysaccharide nanocrystals are advantageously obtained from the isolated crystalline part by removing the amorphous part of the polysaccharide.

From the selected starting material, polysaccharide nanocrystals are prepared by a process advantageously selected from one of the following processes: mechanical fractionation, mild chemical hydrolysis and dissolution/recrystallization.

By "mechanical fractionation", it is meant conventional operation of high pressure homogenization.

By "mild chemical hydrolysis", it is meant a treatment by an acid chemical compound of the polysaccharide, in conditions ensuring its amorphous part removal.

The acid chemical compound is advantageously selected from sulfuric acid or hydrochloric acid.

As described hereinafter in the examples, depending on the acid type, temperature and hydrolysis time, the surface charge can be modulated.

By "dissolution/recrystallization", it is meant acid or basic treatment or solvent treatment, for example phosphoric acid, urea/NaOH, ionic liquids, etc., followed by recrystallization. Such a process is for example described in A. Osorio-Madrazoa et al., Carbohydrate Polymers 83(4), (2011), 1730-1739.

Before their inclusion in the composition, the obtained polysaccharide nanocrystals may be subjected to a post-modification process, at the end of which their surface charge density and/or their hydrophilicity are modified, provided that the post-modification does not generate only hydrophobic nanocrystals.

This post-modification is intended to optimize nanocrystal surface characteristics, especially according to the emulsion in which they are introduced, so that its stabilization is optimized.

In order to modify the chitin surface charge density, the post-modification process consists advantageously in a previously described 2 to 4 h NaOH treatment (Y. M. Fan, T. Saito and A. Isogai, Carbohydrate Polymers, 2010, 79, 1046-1051).

In order to modify the hydrophobicity and the surface charge of neutral polysaccharide nanocrystals, the post-modification process is advantageously intended to generate N-acetyl glucosamine moieties in these polysaccharide nanocrystals.

Alternatively and preferably, the obtained polysaccharide nanocrystals show no change in surface charge, such as previously developed.

As an indication, chitin nanocrystals provided in the step a) of the process for obtaining MIPE or HIPE emulsion according to the invention are advantageously obtained by a manufacture process from chitin.

The step of incorporating polysaccharide nanocrystals in the aqueous phase corresponds to the steps implemented for the incorporation of colloidal particles during the Pickering emulsion manufacture.

"Sequential" or "Two Step" Process

According to an embodiment called "sequential" or "in two steps", the operation c) for forming the emulsion composition by dispersing the hydrophobic phase in the hydrophilic phase consists of two successive steps:

c.1) a step of dispersing said hydrophilic phase in said hydrophobic phase, with a volume ratio hydrophobic phase/hydrophilic phase of at least 5/95, for obtaining intermediate oil-in-water emulsion of the Pickering type, followed by c.2) a step of obtaining the emulsion composition of interest having a percentage of internal phase higher than 50%, where appropriate, of the MIPE or HIPE type, comprising:

c.2.1) a step of adding a volume of hydrophobic phase to the intermediate emulsion composition obtained in step c.1), and stirring of the thus obtained mixture, and/or c.2.2) a step of concentrating the emulsion composition obtained in step c.1) by removing at least a part of said hydrophilic phase.

Provision of an Intermediate Oil-in-Water Emulsion of the Pickering Type, Stabilized by Polysaccharide Nanocrystals The Pickering intermediate emulsion used for obtaining a MIPE or HIPE emulsion according to the invention consists in a composition in emulsion form comprising a hydrophobic phase dispersed in an aqueous phase, and containing emulsifying particles (or in other words, called "emulsioning particles") comprising nanocrystals of a polysaccharide other than cellulose.

As already specified, Pickering emulsion is of the "oil-in-water" type.

The nanocrystals implemented, as well as the hydrophobic and hydrophilic phases used, are as developed above.

Pickering emulsion is thus stabilized by at least nanocrystals of a polysaccharide other than cellulose, advantageously chitin nanocrystals.

According to a preferred embodiment, the intermediate Pickering emulsion composition is only stabilized by nanocrystals of a polysaccharide other than cellulose, advantageously chitin nanocrystals, without adding another emulsifying or stabilizing compound.

The composition comprises advantageously 0.5% by weight of nanocrystals of a polysaccharide other than cellulose, advantageously chitin nanocrystals, based on the total weight of said Pickering emulsion.

As developed above, it was shown according to the invention that an amount of nanocrystals of a polysaccharide other than cellulose, sufficient for obtaining a covering rate of at least 50%, depending on the type of nanocrystals implemented, is required for the preparation of a Pickering emulsion composition suitable for obtaining a final MIPE or HIPE emulsion composition according to the invention.

In the step c.1), the Pickering-type oil-in-water emulsion has advantageously the volume ratio hydrophobic phase/hydrophilic phase of advantageously at least 5/95, and preferably, of at most 50/50, or at most 60/40.

By "at least 5/95", it is meant a minimum value of 5 for the hydrophobic phase in the volume ratio.

By "at most 50/50" or "at most 60/40", it is meant the maximum value of 50 or 60, respectively, for the hydrophobic phase in the volume ratio.

In this context, the volume ratio hydrophobic phase/hydrophilic phase is advantageously selected from 5/95, 10/90, 15/85, 20/80, 25/75, 30/70, 35/65, 40/60, 45/55, 50/50, 55/45 or 60/40.

This Pickering-type oil-in-water emulsion according to the invention has advantageously a percentage of internal phase of less than or equal to 50%.

In this context, the Pickering-type oil-in-water emulsion advantageously comprises a percentage of internal phase ranging between 5 and 30%.

Process of Obtaining the Pickering Emulsion Composition

The process for manufacturing the Pickering intermediate emulsion composition advantageously comprises the following steps:

(a) providing nanocrystals of a polysaccharide other than cellulose, advantageously nanocrystals of chitin, such as defined above, and then (b) incorporating said nanocrystals in the aqueous phase of said composition, in a mass amount capable of generating a covering rate of at least 50%, preferably, at least 80%, in said Pickering intermediate emulsion and stabilizing said intermediate emulsion.

The general steps for the manufacture of the intermediate emulsion can be carried out according to conventional procedures, especially used for the manufacture of a Pickering emulsion.

Reference can be particularly made to document Tzoumaki et al., "Oil-in-water emulsions stabilized by chitin nanocrystal particles", Food Hydrocolloids 25 (2011) 1521-1529.

In particular, the step of incorporating polysaccharide nanocrystals in the aqueous phase corresponds to the steps implemented for the incorporation of colloidal particles during the manufacture of Pickering emulsions.

The dispersion of the hydrophobic phase in the hydrophilic phase (containing the stabilizing nanocrystals) can be achieved by any emulsion-producing technique known by the person skilled in the art.

Thus, a technique for obtaining emulsion by ultrasounds may be used, for example, as conventionally performed. A technique for obtaining emulsion by stirring with a homogenizer disperser device of the rotor-stator type, for example a rotor-stator device known as Ultraturrax™, well known by the person skilled in the art, can also be used.

As an illustration, Pickering emulsion stabilized with chitin nanocrystals can be obtained by subjecting a mixture (i) hydrophilic phase/(ii) hydrophobic phase (said mixture comprising the suitable amount of chitin nanocrystals) to a homogenization step by ultrasounds for a few seconds to a few minutes depending on the power of the device and the volume of emulsion.

Also as an illustration, Pickering emulsion stabilized with chitin nanocrystals can be obtained by subjecting a mixture (i) hydrophilic phase/(ii) hydrophobic phase (said mixture comprising the suitable amount of chitin nanocrystals) to a homogenization step by a rotor/stator device of the Heidolph type (Roth—Registered Trademark) at a rate of at least 5000 rpm (revolutions per minute) for a period of 1 to 3 minutes.

Production of the Medium Internal Phase (MIPE) or High Internal Phase (HIPE)-Type Emulsion Composition from the Pickering Intermediate Emulsion If the Pickering intermediate emulsion stability condition is satisfied (step c.1)), the process can be continued through the step(s) to form the MIPE or HIPE emulsion (step c.2)).

According to the invention, MIPE/HIPE emulsion can be obtained:

c.2.1) by adding a volume of hydrophobic phase to the intermediate emulsion composition obtained in step c.1), and/or c.2.2) by concentrating the intermediate emulsion composition obtained in step c.1), by removing at least a part of said hydrophilic phase.

The HIPE emulsion is obtained by achieving a hydrophobic drop concentration exceeding the threshold of "close packing", or theoretical maximum congestion of spheres of the same size, corresponding to a percentage of internal phase higher than 74-75%.

In this regard, without limitation, two routes are possible:
a variable size of internal phase droplets, and
swelling of the internal phase droplets, and then their distortions.

The following examples show that the Pickering emulsion according to the invention provides HIPE emulsion of interest, the internal phase percentage of which is higher than 74-75%.

Addition of a Volume of Hydrophobic Phase

According to a first embodiment, the process can be continued by adding the hydrophobic phase to form the MIPE or HIPE emulsion (step c.2.1)).

To obtain the MIPE or HIPE emulsion according to the invention from a Pickering intermediate emulsion prepared as described above, a desired amount of hydrophobic phase is advantageously added to said emulsion before stirring the mixture Pickering emulsion/added hydrophobic phase.

This added hydrophobic phase may be the same as, or different from, the hydrophobic phase included in order to form the Pickering emulsion.

Surprisingly, the applicant showed that by simply stirring the mixture Pickering intermediate emulsion/added hydrophobic phase with a homogenizer device (e.g. Ultraturrax™), a MIPE or HIPE emulsion can be directly obtained.

As shown in the examples, in a MIPE or HIPE emulsion according to the invention, the ratio value hydrophobic dispersed phase volume/emulsion volume (and therefore also the ratio value hydrophobic dispersed phase volume/hydrophilic continuous phase volume) directly depends on the hydrophobic phase volume added to the starting Pickering emulsion.

As also shown in the examples, it seems that no specific limit exists for the value of the volume ratio hydrophobic dispersed phase/continuous aqueous phase in the HIPE emulsion thus obtained.

In a MIPE or HIPE emulsion according to the invention, the value of the volume ratio hydrophobic dispersed phase/emulsion may be determined in advance, in relation to the hydrophobic phase volume added to the starting Pickering emulsion for the optimum stirring conditions.

The step of stirring the mixture Pickering emulsion/added hydrophobic phase can be easily carried out with a conventional homogenizer/disperser device, for example an Ultraturrax™-type stirring device.

As an illustration, when an Ultraturrax™-type stirring device is used, HIPE emulsion can be obtained by stirring for at least 15 seconds at a rotation speed of at least 5000 rpm, preferably at least 5500 rpm, for a 4 mL container.

The person skilled in the art adapts the conditions of the mixture stirring step on the basis of the instructions in the present description and its general knowledge in the emulsion composition manufacturing field.

For the mixture stirring step, a period of at least 15 seconds includes the periods of at least 20, 25, 30, 35, 40, 45, 50, 55, 60, 65, 70, 75, 80, 90, 95, 100, 1105, 110, 115, 120, 125, 130, 135, 140, 145, 150 seconds.

Where appropriate, the stirring step may last for more than 200 seconds, although this is not useful for obtaining the final HIPE emulsion.

For the stirring step, a stirring force of at least 1000 rpm includes the stirring forces of at least 1050, 1100, 1150, 1200, 1250, 1300, 1350, 1400, 1450, 1500, 1550, 1600, 1650, 1700, 1750, 1800, 1850, 1900, 2000, 2100, 2200, 2300, 2400, 2500, 2600, 2700, 2800, 2900, 3000, 3100, 3200, 3300, 3400, 3500, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 80000, 8100, 8200, 8300, 8400, 8500, 8600, 8700, 8800, 8900, 9000, or at least 10 000 rpm.

Where appropriate, a stirring force higher than 15000 rpm can be applied, although this is not useful for obtaining the final HIPE emulsion.

Preferably, in the general stirring conditions defined above, the stirring force is less than 20000 rpm, in order to prevent the emulsion structure from being altered. The stirring force can be easily adapted by the person skilled in the art in the light of the content of the present description, and where appropriate, its general knowledge. In particular, the stirring force can be adapted by the person skilled in the art on the basis of the starting Pickering emulsion viscosity, and of the viscosity increase during the preparation of the HIPE emulsion, which depends especially on the viscosity of the hydrophobic phase that is added.

In some embodiments, the step of stirring with an Ultraturrax™-type device may be carried out in two phases, respectively a first phase during which a first stirring force is applied and a second phase during which a second stirring force is applied.

As an illustration, the stirring step can be performed with (i) a first stirring phase at 11000 rpm and (ii) a second stirring phase at 15000 rpm, for example, with approximately the same duration for the first and the second stirring phase.

Advantageously, the stirring step of the mixture Pickering emulsion/added hydrophobic phase is carried out at room temperature, i.e. generally at a temperature of from 15° C. to 25° C., and usually from 18° C. to 23° C.

Concentration of the Emulsion Composition

According to a second embodiment, the process can be continued with a concentration step, in order to form the MIPE or HIPE emulsion (step c2.2)).

This concentration step leads to the removing of the hydrophilic continuous phase by a suitable technique, selected for example from:
creaming/gravity sedimentation,
centrifugation (for example 2000 g for 10 minutes),
filtration (advantageously conventional porous membrane system or continuous ultrafiltration),
osmotic methods,
cryoconcentration methods or drying (in conditions where only the continuous phase is evaporated).

As shown in the examples, in a MIPE or HIPE emulsion according to the invention, the value of the ratio hydrophobic dispersed phase volume/emulsion volume depends particularly on:
the concentration of each of the constituents (hydrophilic phase, hydrophobic phase, nanocrystals),
the process of obtaining the emulsion (ultrasound, rotor stator, etc.), and the conditions used (speed, time period, temperature, energy, volume, etc.).

Parameters of these techniques are adapted as a function of the sample.

Such processes are for example described in the following documents: "Emulsions: Theory and Practice", Paul Becher Third Edition, Oxford University Press 2001 (ISBN 0-8412-3496-5) or "High internal phase emulsions (HIPEs)—Structure, properties and use in polymer preparation", Cameron N R; Sherrington D C, BIOPOLYMERS LIQUID CRYSTALLINE POLYMERS PHASE EMULSION, ADVANCES IN POLYMER SCIENCE, Volume: 126, Pages: 163-214, 1996.

Direct Process

Unexpectedly, the inventors observed that chitin nanocrystals provide a high internal phase emulsion, by directly mixing the hydrophobic phase with the hydrophilic phase (containing the nanocrystals) in suitable proportions.

The dispersion of the hydrophobic phase in the hydrophilic phase can be carried out by any emulsion-forming technique known to the person skilled in the art.

A technique for obtaining an emulsion by ultrasounds can thus be used for example, as it is conventionally carried out. One can also use a technique for obtaining an emulsion by stirring with a homogenizer disperser device of the rotor-stator type, for example, a rotor-stator device known as Ultraturrax™, well known by the person skilled in the art.

As an illustration, an emulsion according to the invention, stabilized with chitin nanocrystals, can be obtained by subjecting the mixture (i) hydrophilic phase/(ii) hydrophobic phase (said mixture comprising the appropriate amount of chitin nanocrystals) to a homogenization step with a rotor/stator device of the Heidolph type (Roth—Registered Trademark) at a speed of 8000 rpm, just until a homogenous emulsion is obtained.

Industrial Applications of a Composition According to the Invention

As it was already mentioned previously in the present description and is illustrated in the examples, a MIPE or HIPE emulsion according to the invention can be obtained with the aim of preparing solid foam or solid emulsion, for example by simply freeze-drying MIPE or HIPE emulsion.

For the preparation of a solid foam, a hydrophobic phase that can be evaporated by freeze-drying is preferentially used. Thus, by subjecting a MIPE or HIPE emulsion of the invention to a freeze-drying step, the hydrophilic phase and the hydrophobic phase are both evaporated so as to obtain a foam formed of a polysaccharide network, said polysaccharide network resulting from the polysaccharide nanocrystals located in the interface hydrophobic phase/hydrophilic phase.

Specifically, the examples illustrate the manufacture of a chitin foam material, by simply freeze-drying a HIPE emulsion according to the invention.

In particular and without limitation, the MIPE type emulsions provide spherical cellular structures, and the HIPE type emulsions provide non-spherical cellular structures.

The solid foam can be used as solid support in various industrial applications, including as thermal or acoustic insulation material, or even as biomaterial support.

The resulting product, i.e. the polysaccharide foam, has a large surface area of polysaccharide material, and can be used especially as a support for active ingredient(s), for example as a support for human or veterinary pharmaceutical active ingredient(s).

As an illustration, such supports of pharmaceutical interest can be obtained when the active ingredient(s) (is) are previously added to the MIPE or HIPE emulsion, either in the hydrophobic phase or in the hydrophilic phase, depending on the hydrophilicity characteristics of the relevant active ingredient(s).

In some embodiments, said polysaccharide supports can comprise both (i) one or more hydrophobic active ingredient(s), (ii) one or more hydrophilic active ingredient(s) and, where appropriate, (iii) one or more amphiphilic active ingredient(s).

In these embodiments, each active ingredient can be added (i) either in one of the hydrophilic or hydrophobic phases used for the preparation of the emulsion composition, (ii) or in the Pickering emulsion used for obtaining the final MIPE or HIPE emulsion in the case of a "sequential" process, (iii) or even in the hydrophobic phase which is added in the step c) of the "sequential" process to obtain the final MIPE or HIPE emulsion.

The object of the invention is therefore to provide a process for preparing a solid foam of polysaccharide comprising the following steps:

a) provide a MIPE or HIPE emulsion as defined in the present description, preferably, a MIPE or HIPE emulsion obtained according to the process specified in the present description, b) remove the hydrophilic phase and the hydrophobic phase of said MIPE or HIPE emulsion by evaporation, preferably by freeze-drying, in order to obtain the particulate solid foam.

A MIPE or HIPE emulsion according to the invention can also be used for the manufacture of a dry emulsion, by evaporation of the hydrophilic phase, for example by freeze-drying, and maintaining of the hydrophobic phase. In these embodiments, the hydrophobic phase may contain one or more substance(s) of interest, for example, one or more active ingredient(s) of pharmaceutical interest.

A MIPE or HIPE emulsion according to the invention can also be used for the manufacture of porous polymer materials, mainly by adding polymerizable hydrophilic monomers in the aqueous phase, and then polymerizing in situ said hydrophilic monomers.

In other aspects, a MIPE or HIPE emulsion according to the invention can be used for the manufacture of polymer material beads, mainly by adding hydrophobic monomers in the dispersed hydrophobic phase, and then polymerizing said monomers.

Polymer materials can be used as a material for manufacturing medical devices, including support material for active ingredients physiologically active, or support material for medical prostheses.

The techniques of obtaining polymer materials, either porous polymer material blocks, or polymer material beads, from different types of emulsion, are known per se in the state of the art.

In some embodiments, said monomers of interest are already present in the hydrophilic continuous phase or in the hydrophobic dispersed phase that is used for obtaining the emulsion composition according to the invention.

In other embodiments of the "sequential" process, said monomers of interest are present in the hydrophobic phase that is added to the starting Pickering emulsion, in the step of forming the MIPE or HIPE emulsion itself.

In still other embodiments, said monomers of interest are subsequently added to the MIPE or HIPE emulsion that was already obtained.

In still other embodiments, the monomers of interest can be successively added in different steps, in the process for obtaining the MIPE or HIPE emulsion according to the invention and/or after obtaining the MIPE or HIPE emulsion composition according to the invention.

In some embodiments, the polymer(s) are used in combination with one or more crosslinking agents.

In order to polymerize the polymer(s) of interest, one or more suitable polymerization initiator compounds are conventionally added.

As an illustration, the use of emulsions, including oil-in-water HIPE emulsions, for the manufacture of polymer materials, is for example described in the PCT application n° WO 2009/013500 or in the U.S. Pat. No. 6,218,440 and U.S. Pat. No. 4,472,086.

The present invention is further illustrated by, but is not limited to, the following examples.

Example: Preparation of an Oil-in-Water Emulsion Stabilized by Chitin Nanocrystals A. Protocols
Protocol 1: Preparation of Chitin Nanocrystals The process for obtaining chitin nanocrystals is described in documents "In vitro chiral nematic ordering of chitin crystallites", Revol, J.-F.; Marchessault, R. H.; Int. Journal of Biological Macromolecules, 1993, 15, 329-335, and "Structure and chirality of the nematic phase in chitin suspensions" Belamie, E; Davidson, P; Giraud-Guille, M. M. Journal of Physical Chemistry B, 2004, 108 (39), 14991-15000.

More specifically, 4 g of chitin in 80 mL of 3N HCl are boiled for 90 minutes under stirring.

The suspension is then diluted, washed with ultrapure water by successive centrifugations at 10000 rpm for 20 minutes, and dialyzed against 0.01 mM HCl during five days.

The final dispersion, consisting of chitin nanocrystals, is subjected to an ultrasound treatment, filtered on 5 μm, then 1.2 μm, and then stored at 4° C.
Protocol 2: Transmission Electron Microscopy (TEM)

20 μL of a chitin nanocrystal aqueous suspension (0.0025% weight/volume) are deposited on a carbon grid for electron microscopy.

After 2 min, the excess of solvent is absorbed and the sample is labeled by adding 20 μL of uranyl acetate (2% in water); the excess is absorbed after 2 min.

This grid for electron microscope is then oven-dried at 40° C.

The grids were then observed with a transmission electron microscope of the JEOL brand (80 kV).

Protocol 3: Preparation of a H/E Emulsion Stabilized by Chitin Nanocrystals

This H/E emulsion can be prepared according to two different protocols, namely in two steps or in a single step.
a) Protocol in Two Steps A first oil-in-water Pickering emulsion is prepared by using an aqueous phase containing a known concentration of chitin nanocrystals in 0.01 mM HCl and 20 mM NaCl.

The emulsions were prepared by using an 20/80 oil/water ratio from an aqueous phase containing nanoparticles at a concentration of 0.3 wt. %, relative to the volume of aqueous phase (without further dilution).

In a tube, 0.2 mL of hexadecane is added to 0.8 mL of the aqueous suspension; during 5 seconds, the mixture is subjected to a treatment alternating 1 second of ultrasound treatment and 2 seconds of rest.

The HIPE type emulsion is then obtained by adding a chosen volume of hexadecane to the rotor-stator at 5500 rpm during 30 sec to 2 min for 1 to 20 mL, respectively.
(b) Protocol in One Step The aqueous and oil phases are directly placed in the tube.

The HIPE type emulsion is then obtained by mixing with a rotor-stator at 5000 rpm for 30 sec to 2 min.
Protocol 4: Optic Microscopy and Particle Size About 20 μL of the emulsion sample are incorporated into 1 mL distilled water.

The product is mixed by vortexing, and then one drop is deposited on a cover slip to be observed with a microscope.

The diameter and the distribution of the drop sizes are determined with a Malvern MasterSizer device by light diffraction with a granulometer Malvern 2000 equipped with a laser He—Ne (Malvern Instruments, U.K.), with Fraunhofer equation analysis.

In this case, the risk of aggregation is limited by adding 0.1% SDS (Sodium Dodecyl Sulfate) and 0.01 mM HCl immediately prior to measurement.
Protocol 5: Scanning Electron Microscopy (SEM)

To prepare emulsion sample for its observation with a scanning electron microscope (SEM), 150 μL of a mixture styrene/initiator (ratio st:AIBN (azobisisobutyronitrile) 100:1 weight/weight) are admixed with 1.0 to 1.5 mL of a 0.3% solution of 0.01 mM HCl sample solution in 20 mM NaCl, previously subjected to ultrasounds for 1-2 min. The mixture is degassed with nitrogen for 10 minutes.

The emulsion was obtained by ultrasound treatment for 30 seconds (2 second impulsions, separated by 5 seconds).

This system is degassed with nitrogen for 10 minutes, and the polymerization is carried out at 50° C., between 6 h and 24 h without stirring.

The resulting preparation is rinsed with 0.01 mM HCl by repeated centrifugations, and then subjected to a metallization step by conventional scanning electron microscopy techniques, prior to observation.
Protocol 6: Internal Phase Percentage Calculation The internal phase percentage is equal to the emulsion oil volume divided by the total volume of the emulsion.

This volume can be obtained for example by sampling, weighing or measuring the emulsion height in a tube of known diameter.
Protocol 7: Deacetylation/Deacetylation The chitin nanocrystal deacetylation process is described in Fan et al., Carbohydrate polymers, 2012, 79, 1046-1051.

More specifically, 240 mL of 40% NaOH are added to 50 mL of 1.2% chitin nanocrystal suspension containing 0.3 g of $NaBH_4$. The mixture is stirred 3 h at 90° C.

After 3 h washing by repeated centrifugations, a dialysis against 0.01 mM HCl and filtration at 5 μm and then 1 μm are implemented.

Protocol 8: Preparation of Solid Foams

Emulsions in 10 mL tubes are centrifuged at 2000 g for 2 to 5 min.

This step allows us to concentrate emulsions and to degas them.

When the centrifugation is completed, the bottom of the tube is cut using a tube cutter for draining all the aqueous phase and recovering only the concentrated emulsion.

The emulsions are then placed in the freezer at −18° C. and freeze-dried.

Protocol 9: Preparation of Dry Foams

Foam-forming assays were performed based on the protocol described in document Alargova et al.—"Foam super-stabilization by polymer microrods", Langmuir, vol. 20(24), 2004, 10371-10374.

This process consists in an aeration by strong manual side stirring of 2 mL of a suspension in a 10 mL measuring cylinder for 30 seconds to 1 minute.

The volume of formed foam is measured in the measuring cylinder by measuring the foam thickening with an electronic caliper. All the measurements were made by the same experimenter.

B. Results

B.1. Evolution of the Mean Diameter as a Function of Different Parameters for the Pickering Emulsions A method for assessing the stability of an emulsion is to measure the droplet size to check for coalescence.

The mean diameter was therefore measured by granulometry (Protocol 4).

(a) Chitin Nanocrystal Concentration

The obtained results are shown in the table 1 below and in FIG. 1.

TABLE 1

Evolution of the mean diameter as a function of the chitin nanocrystal concentration, in a 20 mM NaCl and 0.01 mM HCl solution

| Nanocrystal concentration (g/L) | D3.2 (μm) | D4.3 (μm) | Polydispersity |
|---|---|---|---|
| 0.5 | 11.45 ± 0.64 | 13.25 ± 0.49 | 1.51 |
| 1 | 8.51 ± 0.21 | 10.06 ± 0.57 | 1.58 |
| 2 | 6.67 ± 0.12 | 8.76 ± 0.21 | 1.31 |
| 3 | 5.21 ± 0.16 | 6.96 ± 0.36 | 1.34 |
| 5 | 4.54 ± 0.07 | 6.19 ± 0.10 | 1.36 |

Based on these results, there is a continuous decrease of the diameter with the increase of the introduced chitin nanocrystal number, and then stabilization.

A preferred value for the chitin nanocrystal concentration would be 3 g/L.

(b) Change in pH

Figure 2:
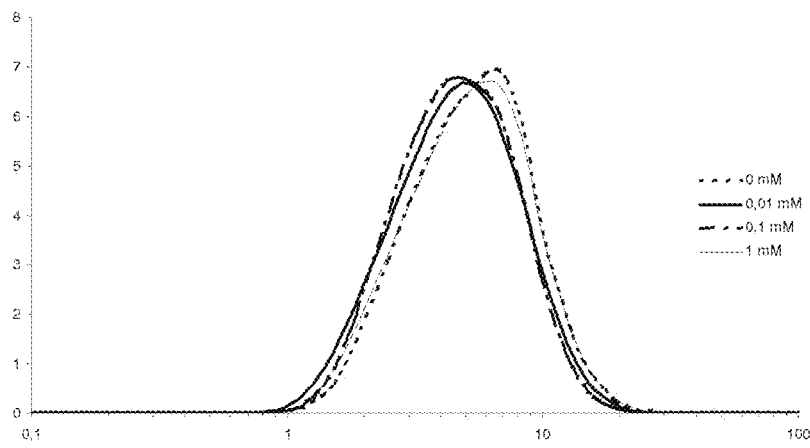
FIG. 2: Drop diameter distribution (μm) as a function of the medium pH, adjusted by the HCl concentration change (3 g/L chitin nanocrystals, 20 mM NaCl)

The results obtained are shown in table 2 below and in FIG. 2.

TABLE 2

Evolution of the mean diameter (μm) as a function of the pH adjusted by HCl concentration (for the 3 g/L emulsions of chitin nanocrystals in a 20 mM NaCl solution)

| HCl concentration (mM) | D3.2 (μm) | D4.3 (μm) | Polydispersity |
|---|---|---|---|
| 0 | 5.83 ± 0.17 | 7.61 ± 0.18 | 1.31 |
| 0.01 | 5.21 ± 0.16 | 6.96 ± 0.36 | 1.34 |
| 0.1 | 5.10 ± 0.15 | 6.58 ± 0.22 | 1.29 |
| 1 | 5.78 ± 0.22 | 7.60 ± 0.27 | 1.32 |

These results show that the pH has no effect on the preparation of Pickering emulsions from chitin nanocrystals.

A preferred value of the pH would be 0.01 to 0.1 mM of HCl.

(c) Change in Salinity

The results obtained are shown in table 3 below.

TABLE 3

Evolution of the mean diameter (μm) as a function of the salinity (mM) by varying the NaCl concentration (for the 3 g/L emulsions of chitin nanocrystals and a HCl concentration of 0.01 mM)

| NaCl concentration (mM) | D3.2 (μm) | D4.3 (μm) | Polydispersity |
|---|---|---|---|
| 0 | 8.32 ± 0.32 | 13.00 ± 0.13 | 1.56 |
| 2 | 5.84 ± 0.16 | 7.53 ± 0.38 | 1.29 |
| 5 | 5.85 ± 0.08 | 7.32 ± 0.34 | 1.25 |
| 10 | 6.23 ± 0.10 | 8.03 ± 0.16 | 1.29 |
| 20 | 6.43 ± 0.21 | 8.43 ± 0.32 | 1.31 |
| 50 | 6.39 ± 0.20 | 8.25 ± 0.35 | 1.29 |
| 100 | 5.35 ± 0.24 | 7.02 ± 0.37 | 1.31 |

In the absence of ionic strength, emulsion production is possible but found to be less controlled and the droplet size distribution more polydisperse.

From a NaCl concentration of 2 mM in our conditions, there is no effect of the ionic strength.

A preferred value would be 20 or 50 mM of NaCl, according to the surface charge density and the concentration.

(d) Storage Stability at Different Temperatures

Samples in our standard conditions (3 g/L of chitin nanocrystals in 20 mM NaCl and 0.01 mM HCl) were stored for a week at different temperatures.

Figure 3:
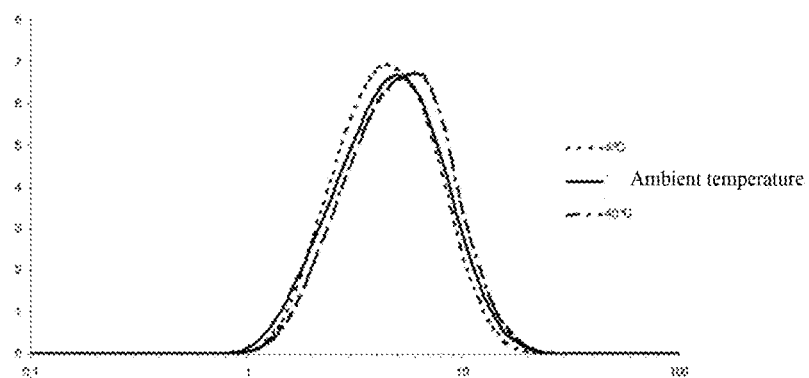
FIG. 3: Drop diameter distribution (μm) after storage at various temperatures (3 g/L chitin nanocrystals, 0.01 mM HCl, 20 mM NaCl)

The results obtained are shown in table 4 below and in FIG. 3.

TABLE 4

Evolution of the mean diameter (μm) as a function of the storage temperature (° C.)

| Storage temperature | D3.2 (μm) | D4.3 (μm) | Polydispersity |
|---|---|---|---|
| 25° C. | 5.21 ± 0.16 | 6.96 ± 0.36 | 1.34 |
| 4° C. | 4.94 ± 0.18 | 6.36 ± 0.23 | 1.29 |
| 40° C. | 5.60 ± 0.15 | 7.10 ± 0.08 | 1.27 |

After these heat treatments, the emulsions remained obviously unchanged.

The value at 25° C. is used as a reference value and the absence of coalescence shows the stability of the emulsions in these conditions.

B.2. Stability on Drying for the Application as Dry Emulsion

A 5 g/L emulsion sample of chitin nanocrystals in 50 mM NaCl and 0.01 mM HCl was maintained in an unplugged tube at 50° C. for 8 h and then at 25° C. for 5 days (time required to dry homogenously).

It was then dispersed again in 0.01 mM HCl and passed on a granulometer.

Figure 4:
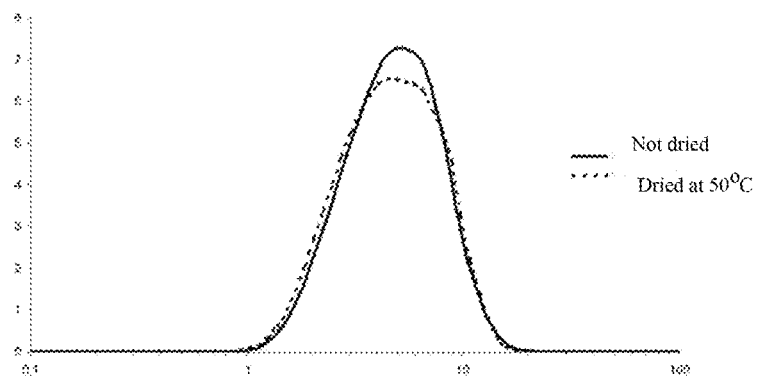
FIG. 4: Drop diameter distribution (μm), before and after drying (5 g/L chitin nanocrystals, 0.01 mM HCl, 50 mM NaCl)

The results obtained are shown in table 5 below and in the appended FIG. 4.

TABLE 5

Evolution of the mean diameter (μm) before and after drying

|  | D3.2 (μm) | D4.3 (μm) | Polydispersity |
|---|---|---|---|
| Not dried | 5.07 ± 0.04 | 6.33 ± 0.07 | 1.25 |
| Dried at 50° C. and then 25° C. | 5.05 ± 0.13 | 6.50 ± 0.35 | 1.29 |

The drop diameter is identical, showing the ability to form dry emulsions.

B.3. Evolution of the Percentage of Internal Phase as a Function of Different Parameters for HIPEs Produced by 2 Protocols ("Direct" and "Two Steps)

The emulsions are prepared in accordance with the above protocols and, after a waiting time of 24 h, the volumes are measured to calculate the percentages of internal phase (Protocol 6).

Finally, the tubes are tilted, or inverted, to give an indication of the texture: S: solid, P: pourable, L: liquid.

The results obtained are developed in tables 6 to 9 below.

TABLE 6

Evolution in our reference conditions: 3 g/L chitin nanocrystals in the 20 mM NaCl and 0.01 mM HCl aqueous phase

| | V oil added (mL) | | | | | | | |
|---|---|---|---|---|---|---|---|---|
| | 0.5 | 1 | 1.5 | 2.5 | 4 | 9 | 15 | 20 |
| % internal phase "two steps" | 70.2 ± 1.3 S | 76.8 ± 0.7 S | 74.3 ± 3.1 S | 77.0 ± 0.0 S | 83.6 ± 0.1 S | 91.6 ± 0.1 S | 94.4 ± 0.1 S | 94.9 ± 0.3 S/P |
| % internal phase direct | 64.2 ± 5.1 S | 64.7 ± 0.6 S | 68.0 ± 0.0 S | 77.1 ± 0.0 S | 83.9 ± 0.0 S | 91.6 ± 0.2 S | 94.9 ± 0.0 S | 84.8 S |

TABLE 7

Evolution as a function of the pH, at higher acidity: 3 g/L chitin nanocrystals in the 20 mM NaCl and 0.01 mM HCl aqueous phase

| | V oil added (mL) | | | | | | | |
|---|---|---|---|---|---|---|---|---|
| | 0.5 | 1 | 1.5 | 2.5 | 4 | 9 | 15 | 20 |
| % internal phase « two steps » | 72.6 ± 4.3 S | 74.2 ± 0.5 S | 75.1 ± 1.1 S | 76.9 ± 0.1 S | 83.6 ± 0.0 S | 91.3 ± 0.3 S | 94.2 ± 0.1 S | 96.1 ± 0.0 S/P |
| % internal phase direct | 69.8 ± 1.9 S | 67.8 ± 0.9 S | 67.7 ± 0.1 S | 76.7 ± 0.1 S | 83.6 ± 0.0 S | 91.5 ± 0.0 S | 94.5 ± 0.4 S | 96.0 S |

TABLE 8

Evolution as a function of the salinity, in the absence of NaCl: 3 g/L chitin nanocrystals in the 0.01 mM HCl aqueous phase

| | V oil added (mL) | | | | | | | |
|---|---|---|---|---|---|---|---|---|
| | 0.5 | 1 | 1.5 | 2.5 | 4 | 9 | 15 | 20 |
| % internal phase « two steps » | 70.3 ± 0.2 P | 74.6 ± 3.3 P | 77.7 ± 3.3 P | 77.6 ± 3.1 S | 83.0 ± 0.0 S | 91.7 ± 0.1 S | 94.6 ± 0.0 S | 95.6 ± 0.8 S/P |
| % internal phase direct | 72.3 ± 3.4 L | 69.7 ± 1.1 L | 71.8 ± 2.0 L | 83.7 ± 4.6 P | 83.5 ± 0.2 S | 91.9 ± 0.3 S | 94.6 ± 0.1 S | 96.0 ± 0.1 S/P |

TABLE 9

Evolution as a function of the salinity, high concentration of NaCl: 3 g/L chitin nanocrystals in the aqueous phase with 100 mM NaCl and 0.01 mM HCl

| | V oil added (mL) | | | | | | | |
|---|---|---|---|---|---|---|---|---|
| | 0.5 | 1 | 1.5 | 2.5 | 4 | 9 | 15 | 20 |
| % internal phase « two steps » | 67.1 ± 5.1 S | 70.2 ± 1.2 S | 69.8 ± 1.8 S | 76.9 ± 0.1 S | 82.2 ± 2.1 S | 91.3 ± 0.1 S | 94.3 ± 0.3 S | 93.4 ± 0.2 S/P |
| % internal phase direct | 40.7 ± 0.3 P | 60.0 ± 0.0 S | 68.0 ± 0.0 S | 77.1 ± 0.1 S | 83.6 ± 0.0 S | 91.7 ± 0.0 S | 94.8 ± 0.0 S | 95.9 ± 0.2 S/C |

If differences are observed for the first less stable and less structured emulsion points in the absence of salt (flowing gel/solid gel), beyond about 74% of internal phase, all the emulsions have an equal percentage of internal phase, regardless of the method and the parameters tested.

In most cases, a solid gel is obtained.

Only the absence of salt results in less structured emulsions, but it is always possible to form HIPEs. At high salinity, the gel being highly structured, it is more difficult to be implemented.

The "direct" route incorporates all of the water introduced, while the "two step" route tends to exclude water, thus increasing the percentage of internal phase for the MIPEs.

Beyond about 74% of internal phase, the percentages of internal phase are the same for the two processes.

However, a noticeable difference in texture is noted between the two methods. The gel structuring seems therefore to be different according to the preparation mode.

If we want a more structured gel (solid gel) and higher percentage of internal phase, it is preferred to use the two step route.

Furthermore, results (not shown) highlight that it is possible to prepare MIPEs and HIPEs from chitin nanocrystals after 1 and 2 hours of deacetylation according to protocol 7.

B.4. Preparation of Solid Foams from Pickering Emulsion or MIPE

The emulsions prepared based on chitin nanocrystals and cyclohexane are frozen and then freeze-dried (Protocol 8).

This protocol provides cellular foams the cell sizes of which are controllable on the basis of the internal phase volume (cyclohexane) added to a Pickering emulsion.

SEM images show these cellular structures. This illustrates the great stability of chitin nanocrystals at the interface, which allows to keep the structure for a very high porosity and extremely thin walls, namely in the range of 10 to 50 nanometers.

These results are related to the properties of the Pickering emulsions because the irreversible adsorption at the interface and the great stability of the emulsions enable the structure to be maintained upon freezing.

For a two step route (results not shown), the structure of the foam is similar.

B.5. Combination of Polysaccharide Nanocrystals

Mixed emulsions of nanocrystals chitin/cellulose were prepared according to the above protocol 3(a) in "two steps", so as to obtain a combination of 1.5 g/L chitin nanocrystals and 1.5 g/L cellulose nanocrystals in the aqueous phase containing 20 mM NaCl and 0.01 mM HCl.

After a waiting time, the volumes are measured to calculate percentages of internal phase (Protocol 6).

Finally, the tubes are tilted, or inverted, to give an indication of the texture: S: solid, P: pourable, L: liquid.

Figure 5:
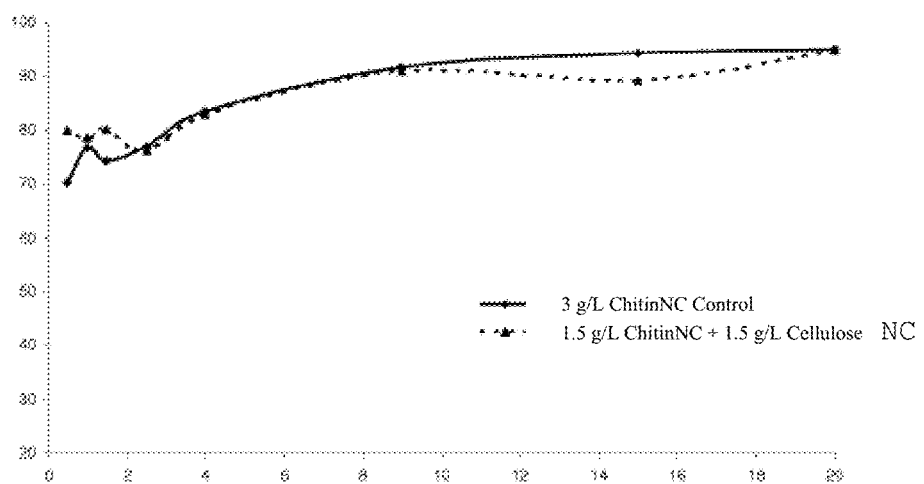
FIG. 5: Change of the internal phase percentage for a mixed suspension 1.5 g/L chitin nanocrystals/1.5 g/L cellulose nanocrystals ("1.5 g/L ChitinNC+1.5 g/L CelluloseNC"), compared with a control suspension of 3 g/L chitin nanocrystals ("3 g/l ChitinNC Control"), as a function of the oil volume added in mL.

The results obtained are developed in table 10 below and in the appended FIG. 5.

The properties remain unchanged, only the nature of the interface is modified.

A suspension including 50% chitin nanocrystals and 50% cellulose nanocrystals leads to MIPEs and HIPEs equivalent in texture and in percentage of internal phase to a suspension comprising 100% of chitin nanocrystals, but whose surface charges will be both positive and negative, which may be interesting for some applications.

B.6. Formation of Stable Dry Foam

Dry foam forming assays were implemented according to the above protocol 9.

The following different parameters were studied:
chitin nanocrystal concentration of 2 g/L to 13 g/L,
ionic strength between 0 and 5 mM of NaCl,
pH at 0.01 mM HCL (pH5), 0.1 mM HCl (pH4) and 1 mM HCl (pH3).

Chitin Concentration

The results obtained are shown in table 11 below, as foam volume fraction relative to the total emulsion volume.

TABLE 11

Comparison of the foam fractions according to the chitin nanocrystal concentrations and stability over time (0.01 mM HCl, 2 mM NaCl)

| | | Chitin nanocrystal concentration (g/L) | | | |
|---|---|---|---|---|---|
| | | 2 | 6 | 10 | 13 |
| Time | 0 | 25% | 41% | 47% | 89% |
| | 2 min | 21% | 33% | 41% | 78% |
| | 20 min | 10% | 30% | 40% | 76% |
| | 12 h | 10% | 29% | 40% | 75% |
| | 2 days | 8% | 23% | 28% | 61% |
| | 5 days | 4% | 22% | 25% | 55% |

Foam formation is actually observed from a chitin nanocrystal concentration of 6 g/L. For concentrations lower than 6 g/L, the foam is very weak and unstable.

Ionic Strength and pH

The results obtained are shown in table 12 below.

TABLE 12

Comparison of the evolutions of foam volume fractions in percentage, according to the ionic strength and pH conditions at 13 g/L of chitin nanocrystals and T = 20 min

| | | NaCl (mM) | | | |
|---|---|---|---|---|---|
| | | 0 | 1 | 2 | 5 |
| HCl (mM) | 0.01 | 67% | 79% | 76% | 70% |
| | 0.1 | 32% | 41% | 61% | 40% |
| | 1 | 0.03% | 0.7% | 28% | 25% |

As shown by the evolutions of foam volume measured, the absence of ionic strength (0 mM NaCl) does not enable

TABLE 10

Evolution of the percentage of internal phase for a mixed suspension chitin/cellulose

| | V oil added (mL) | | | | | | | |
|---|---|---|---|---|---|---|---|---|
| | 0.5 | 1 | 1.5 | 2.5 | 4 | 9 | 15 | 20 |
| % internal phase in "two steps" | 79.9 ± 5.4 | 78.6 ± 1.6 | 80.2 ± 2.1 | 76.2 ± 0.1 | 82.9 ± 0.1 | 91.0 ± 0.2 | 89.3 ± 7.1 | 94.9 ± 0.5 |
| | S | S | S | S | S | S | S | P | foam formation for pH lower than 4. Similarly, the increase of ionic strength beyond 10 mM tends to a foam destabilization regardless of the pH.

Furthermore, the increase of the pH from 3 to 5 promotes foam stabilization.

It was also observed that original foam at pH5 disappears at pH2 (by adding 20 μL of 1M HCl); only a crown remains. A foam reforms when returning to pH5 (by adding 20 μL of 1M NaOH).

These results show the reversible nature of the foam as a function of the pH.

Study of the Foam Stability Over Time

A chitin solution of from 2 g/L to 13 g/L (0.01 mM HCl and 5 mM NaCl) is subjected to a horizontal stirring according to the aforementioned protocol 9.

The results obtained are shown in the above table 11.

A very good stability over time is observed.

The invention claimed is:

1. A composition, comprising:
   an internal phase dispersed in a hydrophilic continuous phase, the percentage of the internal phase being higher than 50%, wherein
   said composition contains nanocrystals of a polysaccharide other than cellulose, which are located at an interface between said internal phase and said hydrophilic continuous phase,
   the nanocrystals of a polysaccharide other than cellulose are selected from nanocrystals which are positively charged, and
   the nanocrystals of a polysaccharide other than cellulose comprise chitin nanocrystals which are in the form of anisotropic rods, wherein
   said chitin nanocrystals have not been functionalized or grafted.

2. The composition according to claim 1, wherein the nanocrystals of a polysaccharide comprise:
   (i) exclusively chitin nanocrystals, or
   (ii) chitin nanocrystals, mixed with nanocrystals derived from at least one negatively charged polysaccharide.

3. The composition according to claim 1, wherein the composition is an emulsion or a foam.

4. The composition according to claim 1, wherein said composition is an emulsion (i) of a high internal phase or HIPE, having a percentage of internal phase higher than 75%, or (ii) of a medium internal phase or MIPE, having a percentage of internal phase ranging between 55% and 75%.

5. A product obtained from the composition according to claim 1, selected from dry emulsion, solid foam, porous polymer material or polymer material beads.

6. A process for obtaining the composition of claim 1, which process comprises the following operations:
   a) an operation of incorporating nanocrystals of a polysaccharide other than cellulose, in a hydrophilic phase,
   b) an operation of providing said hydrophilic phase containing the nanocrystals of a polysaccharide and a phase for constituting said internal phase, and
   c) an operation of forming said composition by dispersing said phase for constituting an internal phase in said hydrophilic phase containing the nanocrystals of a polysaccharide.

7. The process according to claim 6, wherein the nanocrystals of a polysaccharide other than cellulose comprises:
   (i) exclusively chitin nanocrystals, or
   (ii) chitin nanocrystals, mixed with nanocrystals derived from at least one negatively charged polysaccharide.

8. The process according to claim 6, wherein, at the end of the operation c), the obtained composition is an emulsion or a foam.

9. The process according to claim 6, wherein the composition is an emulsion composition, and in that operation c) comprises:
   c.1) a step of obtaining an intermediate oil-in-water emulsion having a volume ratio internal phase/hydrophilic phase of at least 5/95, and
   c.2) a step of obtaining the emulsion composition having a percentage of internal phase higher than 50%, comprising:
      c.2.1) a step of adding a volume of a phase constituting the internal phase to the intermediate oil-in-water emulsion obtained in step c.1), and stirring the mixture thus obtained, or
      c.2.2) a step of concentrating the intermediate oil-in-water emulsion obtained in step c.1) by removing at least a part of said hydrophilic phase.

10. The process according to claim 9, wherein in step c.1), the intermediate oil-in-water emulsion has a percentage of the phase constituting the internal phase of equal to or less than 50%.

11. The process according to claim 6, wherein the composition is an emulsion composition, and in that operation c) consists of mixing the hydrophilic phase containing the nanocrystals of a polysaccharide and the phase for constituting an internal phase to directly obtain said emulsion having a percentage of internal phase higher than 50%.

12. The process according to claim 6, wherein, at the end of operation c), the composition formed is (i) of the high internal phase or HIPE, having a percentage of internal phase higher than 75%, or (ii) of the medium internal phase or MIPE, having a percentage of internal phase ranging between 55% and 75%.

13. The process according to claim 7, wherein the composition is an emulsion composition, and in that operation c) comprises:
   c.1) a step of obtaining an intermediate oil-in-water emulsion having a volume ratio internal phase/hydrophilic phase containing of al least 5/95,
   c.2) a step of obtaining the emulsion composition having a percentage of internal phase higher than 50%, comprising:
      c.2.1) a step of adding a volume of a phase constituting the internal phase to the intermediate oil-in-water emulsion obtained in step c.1), and stirring the mixture thus obtained, or
      c.2.2) a step of concentrating the intermediate oil-in-water emulsion obtained in step c.1) by removing at least a part of said hydrophilic phase.

14. The composition according to claim 1, wherein said chitin nanocrystals have not undergone any surface function modifications.

15. The composition according to claim 1, wherein said chitin nanocrystals have not been modified by deacetylation.

16. The composition according to claim 1, wherein said chitin nanocrystals have not been functionalized or grafted by methacrylate or dimethacrylate.

17. The composition according to claim 1, wherein said chitin nanocrystals have not been functionalized or grafted by polyethylene glycol, poly(hydroxyester) or polystyrene.

18. An emulsion or foam, comprising:
   an internal phase dispersed in a hydrophilic continuous phase, the percentage of the internal phase being higher than 50%, wherein said emulsion or foam contains positively charged anisotropic rods of chitin nanocrystals that have not been functionalized or grafted.

\* \* \* \* \*